(12) United States Patent
Becknell et al.

(10) Patent No.: US 7,732,447 B2
(45) Date of Patent: Jun. 8, 2010

(54) FUSED [D]PYRIDAZIN-7-ONES

(75) Inventors: Nadine C. Becknell, Coatesville, PA (US); Robert L. Hudkins, Chester Springs, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 11/820,887

(22) Filed: Jun. 21, 2007

(65) Prior Publication Data

US 2007/0299061 A1    Dec. 27, 2007

Related U.S. Application Data

(60) Provisional application No. 60/815,717, filed on Jun. 22, 2006.

(51) Int. Cl.
| | |
|---|---|
| C07D 237/26 | (2006.01) |
| A61K 31/4985 | (2006.01) |
| A61P 35/00 | (2006.01) |
| A61P 25/28 | (2006.01) |
| A61P 29/00 | (2006.01) |
| A61P 3/10 | (2006.01) |
| A61P 31/00 | (2006.01) |

(52) U.S. Cl. ........................ 514/248; 544/234
(58) Field of Classification Search .............. 514/228.5, 514/232.8, 248; 544/60, 115, 234
See application file for complete search history.

(56) References Cited

FOREIGN PATENT DOCUMENTS

| EP | 0 512 817 | 2/1997 |
|---|---|---|
| EP | 1 002 535 | 5/2000 |
| JP | 08113574 | 5/1996 |
| WO | WO 03/022849 | 3/2003 |
| WO | WO 2004/035580 | 4/2004 |

OTHER PUBLICATIONS

Nelkin, Annual rept. Jan. 1-Dec. 31, 2006, Johns Hopkins Univ Balt Md.*
Feletar, et al., Drug Discov. Today: Disease Mechan., vol. 5, # 1, Spring 2008, e47-e54.*
Nishiguchi, et al., Investigative Ophthalmol. & Vis. Sci., 2007;48:4315-4320.*
Edirisinghe, et al., The FASEB Journal, 2008;22:2297-2310.*
Dajka-Halasz et al., Tetrahedron 60, 2004, pp. 2283-2291.
Monge et al., An Real Acad. Farm., 1985, 51, pp. 485-493.
Monge et al., Synthesis, 1984, pp. 160-161.
Kogan et al., Khimiko-Farmatsevticheskii Zhurnal, 1974, 8(4), pp. 23-26.
Kogan et al., Khimiya Geterotsiklicheskikh Soedinenii, 1973, 12, pp. 1654-1658.
Kogan et al., Khimiya Geterotsiklicheskikh Soedinenii, 1976, 9, pp. 1218-1222.
Vlasova et al., Khimiya Geterotsiklicheskikh Soedinenii, 1974, 6, pp. 784-787.
Staunton et al., Journal of the Chemical Society, 1953, pp. 1889-1894.
El-Kashef et al., ARKIVOC, 2003, (xiv), pp. 198-209.
Monge et al., Acta Farm. Bonaerense, 1984 3(1), pp. 21-26.
Monge et al., J. Heterocyclic Chem., 1984, 21, pp. 397-400.
Monge et al., Anales de Quimica, 1975, 73, pp. 278-281.
Zhungietu et al., Khimiya Geterotsiklicheskikh' Soedinenii, 1981, 8, pp. 1064-1066.
El-Kashef et al., Molecules, 2004, 9, pp. 849-859.
Ghoneim et al., Bull. Fac. Pharm. Cairo Univ., 2001, 39, pp. 23-31.
Kurumi et al., Heterocycles, 2000, 53(12), pp. 2809-2819.
Bare, J. Heterocyclic Chem., 1998, 35, pp. 1171-1186.
Monge et al., Arch. Pharm., 1995, 328, pp. 689-698.
Stauch Slusher, et al., J. Neural Transm, 1994, 97, pp. 175-185.
Guven et al., Tetrahedron, 1993, 49, pp. 11145-11154.
Monge et al., Arzneim. Forsch./Drug Res. 1993, 43(II), pp. 1175-1180.
Monge et al., Eur. J. Med. Chem., 1991, 26, pp. 655-658.
Monge et al., J. Med. Chem., 1991, 34, pp. 3023-3029.
Monge et al., Journal of Pharmaceutical Science, 1982, 71(12), pp. 1406-1408.
Fernandez-Alvarez, J. Heterocyclic Chem., 1981, 18, pp. 1533-1536.
Hiremath, et al., J. Indian Chem. Soc., 1981 LVII, pp. 782-784.
Kobayashi, et al., Yakugaku Zasshi, 1971, 91(11) pp. 1164-1173.
Huntress et al., Journal of the American Chemical Society, 1941, 63, pp. 2762-2766.

* cited by examiner

Primary Examiner—James O Wilson
Assistant Examiner—Cecilia M Jaisle

(57) ABSTRACT

The present invention is directed to fused [d]pyridazin-7-ones. The invention is also directed to methods for making and using the fused [d]pyridazin-7-ones. In particular, the compounds of the present invention may be effective in the treatment of diseases or disease states related to the activity of VEGFR2, MLK1 and CDK5 enzymes, including, for example, angiogenic disorders and neurodegenerative diseases.

7 Claims, No Drawings

FUSED [D]PYRIDAZIN-7-ONES

FIELD OF THE INVENTION

The present invention is directed to novel multicylic compounds and the use thereof. More particularly, the present invention relates to novel multicyclic compounds and their use, for example, for the inhibition of protein kinase activity.

BACKGROUND OF THE INVENTION

Protein kinases play a critical role in the control of cell growth and differentiation. Aberrant expression or mutations in protein kinases have been shown to lead to uncontrolled cell proliferation, such as malignant tumour growth, and various defects in developmental processes, including cell migration and invasion, and angiogenesis. Protein kinases are therefore critical to the control, regulation, and modulation of cell proliferation in diseases and disorders associated with abnormal cell proliferation. Protein kinases have also been implicated as targets in central nervous system disorders such as Alzheimer's disease, inflammatory disorders such as psoriasis, bone diseases such as osteoporosis, atheroscleroses, restenosis, thrombosis, metabolic disorders such as diabetes, and infectious diseases such as viral and fungal infections.

One of the most commonly studied pathways involving kinase regulation is cellular signaling from receptors at the cell surface to the nucleus. Generally, the function of each receptor is determined by its pattern of expression, ligand availability, and the array of downstream signal transduction pathways that are activated by a particular receptor. One example of this pathway includes a cascade of kinases in which members of the Growth Factor receptor Tyrosine Kinases deliver signals via phosphorylation to other kinases such as Src Tyrosine kinase, and the Raf, Mek and Erk serine/threonine kinase families. Each of these kinases is represented by several family members which play related, but functionally distinct roles. The loss of regulation of the growth factor signaling pathway is a frequent occurrence in cancer as well as other disease states. Fearon, *Genetic Lesions in Human Cancer, Molecular Oncology,* 1996, 143-178.

One receptor tyrosine kinase signaling pathway includes the vascular endothelial growth factor (VEGF) receptor kinase. It has been shown that binding of VEGF to the receptor VEGFR2 affects cell proliferation. For instance, binding of VEGF to the VEGFR-2/flt-1 receptor, which is expressed primarily on endothelial cells, results in receptor dimerization and initiation of a complex cascade which results in growth of new blood vessels (Korpelainen and Alitalo, *Curr. Opin. Cell. Biol.* 1998, 10, 159). Suppression of formation of new blood vessels by inhibition of the VEGFR tyrosine kinases would have utility in a variety of diseases, including treatment of solid tumors, diabetic retinopathy and other intraocular neovascular syndromes, macular degeneration, rheumatoid arthritis, psoriasis, and endometriosis.

The signals mediated by kinases have also been shown to control cell growth, cell death and differentiation in the cell by regulating the processes of the cell cycle. Progression through the eukaryotic cell cycle is controlled by a family of kinases called cyclin dependent kinases (CDKs). The loss of control of CDK regulation is a frequent event in hyperproliferative diseases and cancer.

Inhibitors of kinases involved in mediating or maintaining particular disease states represent novel therapies for these disorders. Examples of such kinases include inhibition of Src, raf, and the cyclin-dependent kinases (CDK) 1, 2, and 4 in cancer, CDK2 or PDGF-R kinase in restenosis, CDK5 and GSK3 kinases in Alzheimers, c-Src kinase in osteoporosis, GSK-3 kinase in type-2 diabetes, p38 kinase in inflammation, VEGF-R 1-3 and TIE-1 and -2 kinases in angiogenesis, UL97 kinase in viral infections, CSF-1R kinase in bone and hematopoietic diseases, and Lck kinase in autoimmune diseases and transplant rejection.

An additional kinase signal transduction is the stress-activated protein kinase (SAPK) pathway (Ip and Davis *Curr. Opin. Cell Biol.* 1998, 10, 205). In response to stimuli such as cytokines, osmotic shock, heat shock, or other environmental stress, the pathway is activated and dual phosphorylation of Thr and Tyr residues within a Thr-Pro-Tyr motif of the c-jun N-terminal kinases (JNKs) is observed. Phosphorylation activates the JNKs for subsequent phosphorylation and activation of various transcription factors, including c-Jun, ATF2 and ELK-1.

The JNKs are mitogen-activated protein kinases (MAPKs) that are encoded by three distinct genes, jnk1, jnk2 and jnk3, which can be alternatively spliced to yield a variety of different JNK isoforms (Gupta et al., *EMBO J* 1996, 15, 2760). The isoforms differ in their ability to interact with and phosphorylate their target substrates. Activation of JNK is performed by two MAPK kinases (MAPKK), MKK4 and MKK7. MKK4 is an activator of JNK as well as an additional MAPK, p38, while MKK7 is a selective activator of JNK. A number of MAPKK kinases are responsible for activation of MKK4 and MKK7, including the MEKK family and the mixed lineage kinase, or MLK family. The MLK family is comprised of six members, including MLK1, MLK2, MLK3, MLK6, dual leucine zipper kinase (DLK) and leucine zipper-bearing kinase (LZK). MLK2 is also known as MST Katoh, et al. *Oncogene,* 1994, 10, 1447). Multiple kinases are proposed to be upstream of the MAPKKKs, including but not restricted to germinal center kinase (GCK), hematopoietic progenitor kinase (HPK), and Rac/cdc42. Specificity within the pathway is contributed, at least in part, by scaffolding proteins that bind selected members of the cascade. For example the JNK interacting protein-1 (JIP-1) binds HPK1, DLK or MLK3, MKK7 and JNK, resulting in a module which enhances JNK activation (Dickens et al. *Science* 1997, 277, 693).

Manipulation of the activity of the SAPK pathway can have a wide range of effects, including promotion of both cell death and cell survival in response to various pro-apoptotic stimuli. For example, down-regulation of the pathway by genetic disruption of the gene encoding JNK3 in the mouse provided protection against kainic acid-induced seizures and prevented apoptosis of hippocampal neurons (Yang et al. *Nature* 1997, 389, 865). Similarly, inhibitors of the JNK pathway such as JIP-1 inhibit apoptosis (Dickens, supra). In contrast, the activity of the JNK pathway appears to be protective in some instances. Thymocytes in which MKK4 has been deleted display increased sensitivity to CD95- and CD3 mediated apoptosis (Nishina et al. *Nature* 1997, 385, 350). Overexpression of MLK3 leads to transformation of NIH 3T3 fibroblasts (Hartkamp et al. *Cancer Res.* 1999, 59, 2195).

An area the present invention is directed toward is identification of compounds that modulate the MLK members of the SAPK pathway and promote either cell death or cell survival. Inhibitors of MLK family members would be anticipated to lead to cell survival and demonstrate therapeutic activity in a variety of diseases, including chronic neurodegenerative diseases such as Alzheimer's disease, Parkinson's disease and Huntington's disease and acute neurological conditions such as cerebral ischemia, traumatic brain injury and spinal injury. Inhibitors of MLK members leading to inhibition of the SAPK pathway (JNK activity) would also display activity in inflammatory diseases and cancer.

Thus, there is a need for novel classes of compounds which demonstrate activity toward receptor and non-receptor types of protein kinases. It has been discovered that a class of compounds, referred to herein as fused [d]pyridazin-7-ones, are useful as agents for the regulation of protein kinases. The present invention is therefore directed to, inter alia, their use as therapeutic agents for the treatment of the foregoing disorders.

SUMMARY OF THE INVENTION

Accordingly, one object of the present invention is to provide novel fused [d]pyridazin-7-ones which are kinase inhibitors. In certain objects, the compounds of the present invention are inhibitors of one or more of vascular endothelial growth factor receptor (VEGFR) kinase, mixed lineage kinase (MLK) or cyclin-dependent kinase (CDK).

It is another object of the present invention to provide pharmaceutical compositions comprising a pharmaceutically acceptable carrier and a therapeutically effective amount of at least one of the compounds of the present invention, or a pharmaceutically acceptable salt form thereof.

It is another object of the present invention to provide a novel method for treating or preventing disorders associated with the aberrant activity of protein kinases. In certain objects, the disorders are characterized by the aberrant activity of one or more of the vascular endothelial growth factor receptor (VEGFR) kinase, mixed lineage kinase (MLK) or cyclin-dependent kinase (CDK), and the method comprises administering to a host in need of such treatment or prevention a therapeutically effective amount of at least one of the compounds of the present invention.

These and other important objects, which will become apparent during the following detailed description, have been achieved by the discovery that compounds of Formula (I):

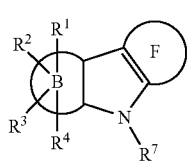

(I)

stereoisomeric forms, mixtures of stereoisomeric forms, or pharmaceutically acceptable salt forms thereof, wherein $R^1$, $R^2$, $R^3$, $R^4$, $R^7$, B and F are defined below, are effective kinase inhibitors.

DETAILED DESCRIPTION OF THE EMBODIMENTS

Thus, in a first embodiment, the present invention provides a novel compound of Formula (I):

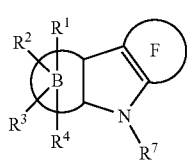

(I)

or a stereoisomer or pharmaceutically acceptable salt form thereof, wherein:

ring B, together with the carbon atoms to which it is attached, is a phenylene ring, wherein 1 or 2 carbon atoms of the phenylene ring are optionally replaced by nitrogen atoms;

ring F is:

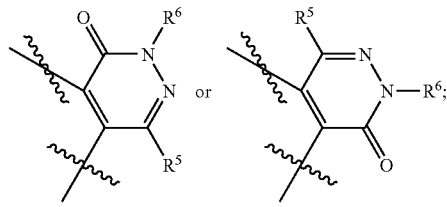

$R^1$ and $R^2$ are independently selected from:
(a) hydrogen, $C_1$-$C_6$ alkyl substituted with 0 to 3 $R^{10}$ groups,
$C_2$-$C_6$ alkenyl substituted with 0 to 3 $R^{10}$ groups,
$C_2$-$C_6$ alkynyl substituted with 0 to 3 $R^{10}$ groups,
$C_6$-$C_{12}$ aryl substituted with 0 to 3 $R^{10}$ groups,
$C_3$-$C_7$ cycloalkyl substituted with 0 to 3 $R^{10}$ groups,
$C_5$-$C_{10}$ heterocyclyl substituted with 0 to 3 $R^{10}$ groups,
$C_5$-$C_{10}$ heteroaryl substituted with 0 to 3 $R^{10}$ groups;
(b) halogen, —$CF_3$, —$CHF_2$, —C≡N, —CHO, —O($CR^a_2$)$_n R^8$, —($CR^a_2$)$_n$C(=O)($CR^a_2$)$_n R^8$, —($CR^a_2$)$_n$C(=O)($CR^a_2$)$_n OR^8$, —($CR^a_2$)$_n$Si($R^8$)$_3$, —($CR^a_2$)$_n NO_2$, —($CR^a_2$)$_n N(R^b)(R^c)$, —($CR^a_2$)$_n$C(=O)N($R^b$)($R^c$), —($CR^a_2$)$_n$OC(=O)N($R^b$)($R^c$), —($CR^a_2$)$_n$OC(=O)($CR^a_2$)$_n R^8$, —($CR^a_2$)$_n N(R^b)$C(=O)$R^8$, —($CR^a_2$)$_n$NC(=O)N($R^b$)($R^c$), —$CR^a_2$)$_n$NC(=O)$OR^8$, —($CR^a_2$)$_n$NS(O)$_x R^8$; and
(c) a group wherein $R^1$ and $R^2$ together form a methylenedioxy or an ethylenedioxy group;

$R^3$ and $R^4$ are independently selected from hydrogen, halogen, $C_1$-$C_4$ alkyl, and —O($CR^a_2$)$_n R^8$;
alternatively, $R^2$ and $R^3$ together form a methylenedioxy or an ethylenedioxy group;

$R^5$ is selected from $C_6$-$C_{12}$ aryl substituted with 0 to 3 $R^9$ groups,
$C_3$-$C_7$ cycloalkyl substituted with 0 to 3 $R^9$ groups,
$C_5$-$C_{10}$ heterocyclyl substituted with 0 to 3 $R^9$ groups, and
$C_5$-$C_{10}$ heteroaryl substituted with 0 to 3 $R^9$ groups;

$R^6$ is selected from hydrogen, —$CH_2 N(R^d)(R^e)$, and the residue of an amino acid after the hydroxyl group of the carboxyl group is removed;

$R^7$ is selected from hydrogen, $C_1$-$C_6$ alkyl substituted with 0 to 3 $R^{10}$ groups,
$C_2$-$C_6$ alkenyl substituted with 0 to 3 $R^{10}$ groups,
$C_2$-$C_6$ alkynyl substituted with 0 to 3 $R^{10}$ groups,
$C_6$-$C_{12}$ aryl substituted with 0 to 3 $R^{10}$ groups,
$C_3$-$C_7$ cycloalkyl substituted with 0 to 3 $R^{10}$ groups,
$C_5$-$C_{10}$ heterocyclyl substituted with 0 to 3 $R^{10}$ groups, and
$C_5$-$C_{10}$ heteroaryl substituted with 0 to 3 $R^{10}$ groups;

$R^8$ is selected from hydrogen, $C_1$-$C_4$ alkyl, $C_2$-$C_4$ alkenyl, $C_2$-$C_4$ alkynyl, $C_6$-$C_{12}$ aryl, $C_3$-$C_7$ cycloalkyl, $C_5$-$C_{10}$ heterocyclyl, and $C_5$-$C_{10}$ heteroaryl;

$R^9$ is selected from:
(a) $C_1$-$C_6$ alkyl, $C_2$-$C_6$ alkenyl, $C_2$-$C_6$ alkynyl, $C_6$-$C_{12}$ aryl, $C_3$-$C_7$ cycloalkyl, $C_5$-$C_{10}$ heterocyclyl, $C_5$-$C_{10}$ heteroaryl,
(b) halogen, —$CF_3$, —$CHF_2$, —C≡N, —CHO, (c) —O(CR$^a_2$)$_n$R$^8$, —(CR$^a_2$)$_n$C(=O)(CR$^a_2$)$_n$R$^8$, —(CR$^a_2$)$_n$C(=O)(CR$^a_2$)$_n$OR$^8$, —(CR$^a_2$)$_n$Si(R$^8$)$_3$, —(CR$^a_2$)$_n$NO$_2$, —(CR$^a_2$)$_n$N(R$^b$)(R$^c$), —(CR$^a_2$)$_n$C(=O)N(R$^b$)(R$^c$), —CR$^a_2$)$_n$OC(=O)N(R$^b$)(R$^c$), —(CR$^a_2$)$_n$OC(=O)(CR$^a_2$)$_n$R$^8$, —(CR$^a_2$)$_n$N(R$^b$)C(=O)R$^8$, —(CR$^a_2$)$_n$NC(=O)N(R$^b$)(R$^c$), —(CR$^a_2$)$_n$NC(=O)OR$^8$, and —(CR$^a_2$)$_n$NS(O)$_x$R$^8$;

R$^{10}$ is selected from C$_1$-C$_6$ alkyl, C$_2$-C$_6$ alkenyl, C$_2$-C$_6$ alkynyl, halogen, and —OR$^{11}$;

R$^{11}$ is selected from hydrogen, C$_1$-C$_4$ alkyl, C$_2$-C$_4$ alkenyl, C$_2$-C$_4$ alkynyl, C$_6$-C$_{12}$ aryl, C$_3$-C$_7$ cycloalkyl, C$_5$-C$_{10}$ heterocyclyl, and C$_5$-C$_{10}$ heteroaryl;

R$^a$ is selected from hydrogen, C$_1$-C$_4$ alkyl, C$_2$-C$_4$ alkenyl, and C$_2$-C$_4$ alkynyl;

R$^b$ and R$^c$ are independently selected from hydrogen, hydroxy, C$_1$-C$_4$ alkyl, C$_2$-C$_4$ alkenyl, and C$_2$-C$_4$ alkynyl;

R$^d$ and R$^e$ are independently selected from:
hydrogen, C$_1$-C$_4$ alkyl, and
a group wherein R$^d$ and R$^e$, together with the nitrogen atom to which they are attached, form

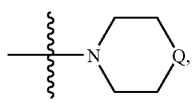

wherein Q is selected from >CH$_2$, oxygen, sulfur and >N(R$^f$);

R$^f$ is hydrogen or C$_1$-C$_4$ alkyl;

n is independently at each occurrence 0, 1, 2, 3 or 4; and x is independently 1 or 2;

with the provisos that:
(a) when ring B is phenylene; R$^1$, R$^2$, R$^3$, R$^4$ and R$^6$ are independently hydrogen; and R$^7$ is hydrogen or methyl; then R$^5$ cannot be phenyl, 4-bromo-phenyl, 4-chloro-phenyl, 4-nitro-phenyl, 4-methyl-phenyl or 4-methoxy-phenyl; and
(b) when ring B is phenylene substituted with one group selected from bromo, methoxy and methyl; and R$^6$ and R$^7$ are hydrogen; then R$^5$ cannot be phenyl or 4-chloro-phenyl.

In certain preferred embodiments of the compounds of Formula (I), ring B is phenylene, R$^5$ is C$_6$-C$_{12}$ aryl substituted with 0 to 3 R$^9$ groups and R$^6$ is hydrogen. In certain further preferred embodiments, R$^1$, R$^2$, R$^3$, and R$^4$ are hydrogen.

In other preferred embodiments of this formula, R$^1$ and R$^2$ are independently-selected from hydrogen, —O(CR$^a_2$)$_n$R$^8$, (CR$^a_2$)$_n$NO$_2$ and a group wherein R$^1$ and R$^2$ together form a methylenedioxy or an ethylenedioxy group. In other preferred embodiments, R$^7$ is selected from hydrogen and methyl.

In certain preferred embodiments of the compounds of Formula (I), ring B is phenylene, R$^5$ is C$_5$-C$_{10}$ heteroaryl substituted with 0 to 3 R$^9$ groups and R$^6$ is hydrogen. In certain further preferred embodiments, R$^1$, R$^2$, R$^3$, and R$^4$ are hydrogen.

In other preferred embodiments of this formula, R$^1$ and R$^2$ are independently selected from hydrogen, —O(CR$^a_2$)$_n$R$^8$, —(CR$^a_2$)$_n$NO$_2$, and a group wherein R$^1$ and R$^2$ together form a methylenedioxy or an ethylenedioxy group. In other preferred embodiments, R$^7$ is selected from hydrogen and methyl.

In other preferred embodiments, the novel compounds are represented by Formula (II):

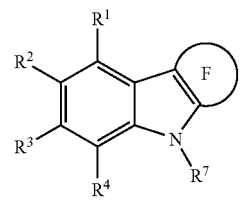

or a stereoisomer or pharmaceutically acceptable salt form thereof.

In other preferred embodiments of this formula, R$^5$ is C$_6$-C$_{12}$ aryl substituted with 0 to 3 R$^9$ groups, R$^6$ is hydrogen and R$^7$ is selected from hydrogen and methyl. In certain further preferred embodiments, R$^1$, R$^2$, R$^3$, and R$^4$ are hydrogen.

In other preferred embodiments, R$^2$ and R$^3$ together form a methylenedioxy or an ethylenedioxy group. In other preferred embodiments, R$^1$ is hydrogen or —O(CR$^a_2$)$_n$R$^1$ and R$^2$, R$^3$ and R$^4$ are hydrogen. In other preferred embodiments, R$^2$ is hydrogen, —O(CR$^a_2$)$_n$R$^8$ or —(CR$^a_2$)$_n$NO$_2$ and R$^1$, R$^3$ and R$^4$ are hydrogen. In other preferred embodiments, R$^3$ is hydrogen or —O(CR$^a_2$)$_n$R$^8$ and R$^1$, R$^2$ and R$^4$ are hydrogen.

In other preferred embodiments of Formula (II), R$^5$ is C$_5$-C$_{10}$ heteroaryl substituted with 0 to 3 R$^9$ groups, R$^6$ is hydrogen and R$^7$ is selected from hydrogen and methyl. In certain further preferred embodiments, R$^1$, R$^2$, R$^3$, and R$^4$ are hydrogen.

In other preferred embodiments, R$^2$ and R$^3$ together form a methylenedioxy or an ethylenedioxy group. In other preferred embodiments, R$^1$ is hydrogen or —O(CR$^a_2$)$_n$R$^8$ and R$^2$, R$^3$ and R$^4$ are hydrogen. In other preferred embodiments, R$^2$ is hydrogen, —O(CR$^a_2$)$_n$R$^8$ or —(CR$^a_2$)$_n$NO$_2$ and R$^1$, R$^3$ and R$^4$ are hydrogen. In other preferred embodiments, R$^3$ is hydrogen or —O(CR$^a_2$)$_n$R$^8$ and R$^1$, R$^2$ and R$^4$ are hydrogen.

In other preferred embodiments of Formula (II), R$^5$ is benzofuranyl substituted with 0 to 3 R$^9$ groups, R$^6$ is hydrogen and R$^7$ is selected from hydrogen and methyl.

Even further preferred embodiments are the compounds set forth in Tables I and II.

In other embodiments, the present invention provides a pharmaceutical composition comprising a compound of Formula (I) and a pharmaceutically acceptable carrier. In other preferred embodiments, the present invention provides a pharmaceutical composition comprising a compound of Formula (II) and a pharmaceutically acceptable carrier. In other preferred embodiments, the present invention provides a pharmaceutical composition comprising a compound from Table I and a pharmaceutically acceptable carrier. In other preferred embodiments, the present invention provides a pharmaceutical composition comprising a compound from Table II and a pharmaceutically acceptable carrier.

In other embodiments, the present invention provides a method of inhibiting a kinase selected from VEGFR2, CDK5 and MLK1, comprising contacting said VEGFR2, CDK5 and MLK1 with a compound of Formula (I):

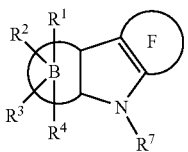
(I)

or a stereoisomer or pharmaceutically acceptable salt form thereof, wherein:
ring B, together with the carbon atoms to which it is attached, is a phenylene ring, wherein 1 or 2 carbon atoms of the phenylene ring are optionally replaced by nitrogen atoms;
ring F is:

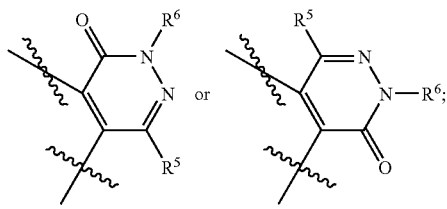

$R^1$ and $R^2$ are independently selected from:
(a) hydrogen, $C_1$-$C_6$ alkyl substituted with 0 to 3 $R^{10}$ groups,
$C_2$-$C_6$ alkenyl substituted with 0 to 3 $R^{10}$ groups,
$C_2$-$C_6$ alkynyl substituted with 0 to 3 $R^{10}$ groups,
$C_6$-$C_{12}$ aryl substituted with 0 to 3 $R^{10}$ groups,
$C_3$-$C_7$ cycloalkyl substituted with 0 to 3 $R^{10}$ groups,
$C_5$-$C_{10}$ heterocyclyl substituted with 0 to 3 $R^{10}$ groups,
$C_5$-$C_{10}$ heteroaryl substituted with 0 to 3 $R^{10}$ groups;
(b) halogen, —$CF_3$, —$CHF_2$, —C≡N, —CHO, —O($CR^a_2$)$_n$$R^8$, —$CR^a_2$)$_n$C(=O)($CR^a_2$)$_n$$R^8$, —$CR^a_2$)$_n$C(=O)($CR^a_2$)$_n$$OR^8$, —($CR^a_2$)$_n$Si($R^8$)$_3$, —($CR^a_2$)$_n$$NO_2$, —$CR^a_2$)$_n$N($R^b$)($R^c$), —($CR^a_2$)$_n$C(=O)N($R^b$)($R^c$), —($CR^a_2$)$_n$OC(=O)N($R^b$)($R^c$), —($CR^a_2$)$_n$OC(=O)($CR^a_2$)$_n$$R^8$, —($CR^a_2$)$_n$N($R^b$)C(=O)$R^8$, —($CR^a_2$)$_n$NC(=O)N($R^b$)($R^c$), —($CR^a_2$)$_n$NC(=O)$OR^8$, —($CR^a_2$)$_n$NS(O)$_x$$R^8$; and
(c) a group wherein $R^1$ and $R^2$ together form a methylenedioxy or an ethylenedioxy group;
$R^3$ and $R^4$ are independently selected from hydrogen, halogen, $C_1$-$C_4$ alkyl, and —O($CR^a_2$)$_n$$R^8$;
alternatively, $R^2$ and $R^3$ together form a methylenedioxy or an ethylenedioxy group;
$R^5$ is selected from $C_6$-$C_{12}$ aryl substituted with 0 to 3 $R^9$ groups,
$C_3$-$C_7$ cycloalkyl substituted with 0 to 3 $R^9$ groups,
$C_5$-$C_{10}$ heterocyclyl substituted with 0 to 3 $R^9$ groups, and
$C_5$-$C_{10}$ heteroaryl substituted with 0 to 3 $R^9$ groups;
$R^6$ is selected from hydrogen, —$CH_2$N($R^d$)($R^e$), and the residue of an amino acid after the hydroxyl group of the carboxyl group is removed;
$R^7$ is selected from hydrogen, $C_1$-$C_6$ alkyl substituted with 0 to 3 $R^{10}$ groups,
$C_2$-$C_6$ alkenyl substituted with 0 to 3 $R^{10}$ groups,
$C_2$-$C_6$ alkynyl substituted with 0 to 3 $R^{10}$ groups,
$C_6$-$C_{12}$ aryl substituted with 0 to 3 $R^{10}$ groups,
$C_3$-$C_7$ cycloalkyl substituted with 0 to 3 $R^{10}$ groups,
$C_5$-$C_{10}$ heterocyclyl substituted with 0 to 3 $R^{10}$ groups, and
$C_5$-$C_{10}$ heteroaryl substituted with 0 to 3 $R^{10}$ groups;

$R^8$ is selected from hydrogen, $C_1$-$C_4$ alkyl, $C_2$-$C_4$ alkenyl, $C_2$-$C_4$ alkynyl, $C_6$-$C_{12}$ aryl, $C_3$-$C_7$ cycloalkyl, $C_5$-$C_{10}$ heterocyclyl, and $C_5$-$C_{10}$ heteroaryl;
$R^9$ is selected from:
(a) $C_1$-$C_6$ alkyl, $C_2$-$C_6$ alkenyl, $C_2$-$C_6$ alkynyl, $C_6$-$C_{12}$ aryl, $C_3$-$C_7$ cycloalkyl, $C_5$-$C_{10}$ heterocyclyl, $C_5$-$C_{10}$ heteroaryl,
(b) halogen, —$CF_3$, —$CHF_2$, —C≡N, —CHO,
(c) —O($CR^a_2$)$_n$$R^8$, —($CR^a_2$)$_n$C(=O)($CR^a_2$)$_n$$R^8$, —($CR^a_2$)$_n$C(=O)($CR^a_2$)$_n$$OR^8$, —($CR^a_2$)$_n$Si($R^8$)$_3$, —($CR^a_2$)$_n$$NO_2$, —($CR^a_2$)$_n$N($R^b$)($R^c$), —($CR^a_2$)$_n$C(=O)N($R^b$)($R^c$), —$CR^a_2$)$_n$OC(=O)N($R^k$)($R^c$), —($CR^a_2$)$_n$OC(=O)($CR^a_2$)$_n$$R^8$, —($CR^a_2$)$_n$N($R^b$)C(=O)$R^8$, —($CR^a_2$)$_n$NC(=O)N($R^b$)($R^c$), —($CR^a_2$)$_n$NC(=O)$OR^8$, and —($CR^a_2$)$_n$NS(O)$_n$$R^8$;
$R^{10}$ is selected from $C_1$-$C_6$ alkyl, $C_2$-$C_6$ alkenyl, $C_2$-$C_6$ alkynyl, halogen, and —$OR^{11}$;
$R^{11}$ is selected from hydrogen, $C_1$-$C_4$ alkyl, $C_2$-$C_4$ alkenyl, $C_2$-$C_4$ alkynyl, $C_6$-$C_{12}$ aryl, $C_3$-$C_7$ cycloalkyl, $C_5$-$C_{10}$ heterocyclyl, and $C_5$-$C_{10}$ heteroaryl;
$R^a$ is selected from hydrogen, $C_1$-$C_4$ alkyl, $C_2$-$C_4$ alkenyl, and $C_2$-$C_4$ alkynyl;
$R^b$ and $R^c$ are independently selected from hydrogen, hydroxy, $C_1$-$C_4$ alkyl, $C_2$-$C_4$ alkenyl, and $C_2$-$C_4$ alkynyl;
$R^d$ and $R^e$ are independently selected from:
(a) hydrogen, $C_1$-$C_4$ alkyl, and
(b) a group wherein $R^d$ and $R^e$, together with the nitrogen atom to which they are attached, form

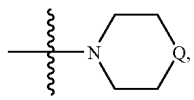

wherein Q is selected from >$CH_2$, oxygen, sulfur and >N(R);
$R^f$ is hydrogen or $C_1$-$C_4$ alkyl;
n is independently at each occurrence 0, 1, 2, 3 or 4; and
x is independently 1 or 2.

In other embodiments of this formula, the present invention provides a method for treating or preventing angiogenic disorders which comprises administering to a host in need of such treatment or prevention a therapeutically effective amount of a compound of Formula (I). In a preferred embodiment, the angiogenic disorder is cancer of solid tumors, endometriosis, diabetic retinopathy, psoriasis, hemangioblastoma, ocular disorders or macular degeneration.

In other embodiments, the present invention provides a method for treating or preventing Alzheimer's disease, amyotrophic lateral sclerosis, Parkinson's disease, stroke, ischaemia, Huntington's disease, AIDS dementia, epilepsy, multiple sclerosis, peripheral neuropathy, injuries of the brain or spinal cord, cancer, restenosis, osteoporosis, inflammation, viral infections, bone or hematopoietic diseases, autoimmune diseases or transplant rejection which comprises administering to a host in need of such treatment or prevention a therapeutic effective amount of a compound of Formula I. In a preferred embodiment, the present invention provides a method of treating or preventing Alzheimer's Disease which comprises administering to a host in need of such treatment or prevention a therapeutic effective amount of a compound of Formula (I).

In other embodiments, the present invention provides for the use of a compound of Formula (I) in the manufacture of a medicament for treating or preventing angiogenic disorders selected from cancer of solid tumors, endometriosis, diabetic retinopathy, psoriasis, hemangioblastoma, ocular disorders and macular degeneration.

In other embodiments, the present invention provides for the use of a compound of Formula (I) in the manufacture of a medicament for treating or preventing Alzheimer's disease, amyotrophic lateral sclerosis, Parkinson's disease, stroke, ischaemia, Huntington's disease, AIDS dementia, epilepsy, multiple sclerosis, peripheral neuropathy, injuries of the brain or spinal cord, cancer, restenosis, osteoporosis, inflammation, viral infections, bone or hematopoietic diseases, autoimmune diseases or transplant rejection.

In other embodiments, the present invention provides for the use of a compound of Formula (I) in the manufacture of a medicament for treating or preventing Alzheimer's disease.

The compounds represented by Formula I may also be referred to as Compound I, and the same applies to the compounds of other formula numbers.

Definitions

The following terms and expressions have the indicated meanings. As used herein "stable compound" or "stable structure" is meant to indicate a compound that is sufficiently robust to survive isolation to a useful degree of purity from a reaction mixture, and preferably capable of formulation into an efficacious therapeutic agent. The present invention is directed only to stable compounds. As used herein, "substituted" is intended to indicate that one or more hydrogen atoms on an indicated group is replaced with a selected group referred to herein as a "substituent", provided that the substituted atom's valency is not exceeded, and that the substitution results in a stable compound. It is understood that substituents and substitution patterns on the compounds of the present invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "alkyl" means a straight-chain, or branched alkyl group having 1 to 6 carbon atoms, such as methyl, ethyl, propyl, isopropyl, butyl, isobutyl, sec-butyl, tert-butyl, pentyl, isoamyl, neopentyl, 1-ethylpropyl, and hexyl.

As used herein, the term "cycloalkyl" is meant to refer to a monocyclic saturated or partially unsaturated hydrocarbon group having 3 to 7 carbon atoms. Examples of cycloalkyl groups include, but are not limited to, cyclopropyl, cyclobutyl, cyclopentyl, cyclohexyl, and cycloheptyl.

As used herein, the term "alkylene" denotes alkyl groups having two points of attachment; i.e., non-terminal alkyl groups. Examples of alkylene groups include methylene, ethylene, propylene, butylene, pentylene and hexylene.

As used herein, the term "alkenyl" is intended to include hydrocarbon chains of either a straight or branched configuration having 2 to 6 carbon atoms and one or more unsaturated carbon-carbon double bonds which may occur in any stable point along the chain, such as ethenyl, propenyl, 3-methylbutenyl, hexenyl and the like.

As used herein, "alkynyl" is intended to include hydrocarbon chains of either a straight or branched configuration having 2 to 6 carbon atoms and one or more triple carbon-carbon bonds which may occur in any stable point along the chain, such as ethynyl, propynyl, 3-methylbutynyl, hexynyl and the like.

As used herein, the term "aryl" is intended to include an aromatic ring having 6 to 12 carbon atoms. Examples of such aryl elements include phenyl, naphthyl, tetrahydronaphthyl, indanyl, or acenaphthyl. In cases where the aryl substituent is bicyclic and one ring is non-aromatic, it is understood that attachment is via the aromatic ring. Included within the definition of "aryl" are fused ring systems, including, for example, ring systems in which an aromatic ring is fused to a cycloalkyl ring.

The term "phenylene", as used herein denotes a phenyl group having two points of attachment; i.e., a non-terminal phenyl group.

The term "heterocyclyl" or "$C_5$-$C_{10}$ heterocyclyl", as used herein, refers to a 5-10 membered monocyclic or bicyclic non-aromatic ring, which may be saturated or partially unsaturated, and which contains, in addition to carbon atoms, at least one heteroatom selected from oxygen, nitrogen, sulfur, selenium, and phosphorus. In addition, the bonds connecting the endocyclic atoms of a heterocyclyl group may be part of a fused aromatic moiety, so long as the heterocyclyl group is not aromatic. Examples of heterocyclyl groups include, but are not limited to, 2-pyrrolidinyl, 3-pyrrolidinyl, piperidinyl, 2-tetrahydrofuranyl, 3-tetrahydrofuranyl, 2-tetrahydrothienyl, 3-tetrahydrothienyl, tetrahydroquinolinyl, and tetrahydroisoquinolinyl.

The term "heteroaryl" or "$C_5$-$C_{10}$ heteroaryl", as used herein, refers to an aromatic ring system having 5 to 10 ring atoms and which contains, in addition to carbon atoms, at least one heteroatom selected from oxygen, nitrogen or sulfur. Non-limiting examples are pyrryl, furanyl, pyridyl, 1,2,4-thiadiazolyl, thiophenyl, isothiazolyl, imidazolyl, tetrazolyl, pyrazinyl, pyrimidyl, quinolyl, isoquinolyl, benzothiophenyl, benzofuranyl, pyrazolyl, indolyl, purinyl, carbazolyl, benzimidazolyl, isoxazolyl, thiazolyl, indazolyl and quinazolyl.

The term "halogen," as used herein is intended to include chloro, fluoro, bromo and iodo.

The term "oxy", as used as a suffix herein denotes attachment through an oxygen atom.

As used herein, the term "amino acid" denotes a molecule containing both an amino group and a carboxyl group. Embodiments of amino acids include α-amino, β-amino, γ-amino acids. As used herein, "α-amino acids" are carboxylic acids of general formula HOOC—CH(NH$_2$)-(side chain). Side chains of amino acids include naturally occurring and non-naturally occurring moieties. Non-naturally occurring (i.e., unnatural) amino acid side chains are moieties that are used in place of naturally occurring amino acid side chains in, for example, amino acid analogs. See, for example, Lehninger, Biochemistry, Second Edition, Worth Publishers, Inc, 1975, pages 73-75, the disclosure of which is incorporated herein by reference. In certain embodiments, substituent groups of substituent $R^6$ include "the residue of an amino acid after the hydroxyl group of the carboxyl group is removed"; i.e., groups of formula —C(=O)CH(NH$_2$)-(side chain).

Functional groups present on the compounds of Formula I or intermediate compounds may also contain protecting groups. Preferred protecting groups include the benzyloxycarbonyl (Cbz; Z) group and the tert-butyloxycarbonyl (Boc) group. Other preferred protecting groups may be found in Greene, T. W. and Wuts, P. G. M., *Protective Groups in Organic Synthesis* 2d. Ed., Wiley & Sons, 1991, a common text in the field, the disclosure of which is incorporated herein by reference.

As used herein, terms commonly used to describe the effects of therapeutic agents in biological systems, assays, and the like, are intended to have their art-recognized meanings. As used herein, the term "effect" when used to modify the terms "function" and "survival" means a positive or negative alteration or change. An effect which is positive may be referred to herein as an "enhancement" or "enhancing", and an effect which is negative may be referred to herein as "inhibition" or "inhibiting."

As used herein, "inhibit" and "inhibition" mean that a specified response of a designated material (e.g., enzymatic activity) is comparatively decreased in the presence of a compound of the present invention.

As used herein, the terms "cancer" and "cancerous" refer to any malignant proliferation of cells in a mammal. Examples include prostate, benign prostate hyperplasia, ovarian, breast, brain, lung, pancreatic, colorectal, gastric, stomach, solid tumors, head and neck, neuroblastoma, renal cell carcinoma, lymphoma, leukemia, other recognized malignancies of the hematopoietic systems, and other recognized cancers.

As used herein the terms "neuron," "cell of neuronal lineage" and "neuronal cell" include, but are not limited to, a heterogeneous population of neuronal types having singular or multiple transmitters and/or singular or multiple functions; preferably, these are cholinergic and sensory neurons. As used herein, the phrase "cholinergic neuron" means neurons of the Central Nervous System (CNS) and Peripheral Nervous System (PNS) whose neurotransmitter is acetylcholine; exemplary are basal forebrain, striatal, and spinal cord neurons. As used herein, the phrase "sensory neuron" includes neurons responsive to environmental cues (e.g., temperature, movement) from, e.g., skin, muscle and joints; exemplary is a neuron from the dorsal root ganglion.

As used herein, a "trophic factor-responsive cell," is a cell which includes a receptor to which a trophic factor can specifically bind; examples include neurons (e.g., cholinergic and sensory neurons) and non-neuronal cells (e.g., monocytes and neoplastic cells).

As used herein, a "therapeutically effective amount" refers to an amount of a compound of the present invention effective to prevent or treat the symptoms of a particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of Formula I.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Synthesis

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate generation of target chiral centers.

As will be readily understood, functional groups present on the compounds of Formula I may contain protecting groups during the course of synthesis. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P. G. M., *Protective Groups in Organic Synthesis* 2d. Ed., Wiley & Sons, 1991.

Compounds of the present invention may be prepared as outlined in the following schemes. Generally, compounds of Examples 4 may be prepared, for example, by methods set forth in Scheme 1.

Scheme 1:

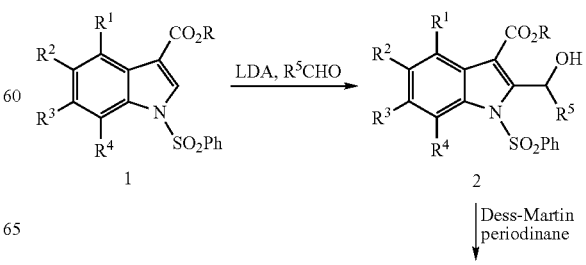

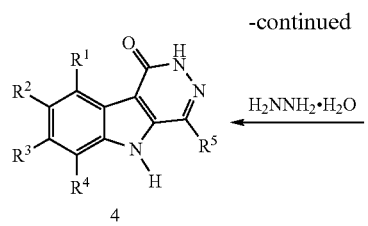 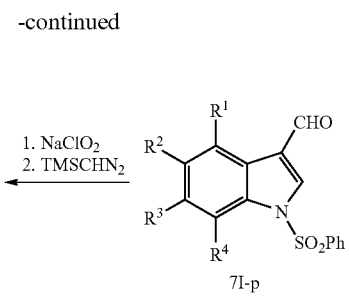

Compounds 1 may be alkylated by first treatment with a base such as lithium diisopropylamide (LDA), and then reacted with an aldehyde or acid chloride to give the corresponding alcohol (2) or ketone (3). Conversion of 2 to 3 may be carried out by using an appropriate oxidizing condition, for example Dess-Martin periodinane (J. Am. Chem. Soc. 1991, 113, 7177.) or Swern conditions (DMSO/TFAA). Reaction of 3 with various hydrazines may produce compounds 4. Example 4q may be obtained by hydrogenation of 4o using an appropriate catalyst, such as 10% palladium on carbon or 20% palladium hydroxide. Reaction of 3 with substituted hydrazines (R—NHNH$_2$) provides a route to N-substituted pyridazinones.

Indole compounds 1l-p may be prepared as outlined in Scheme 2.

Scheme 2:

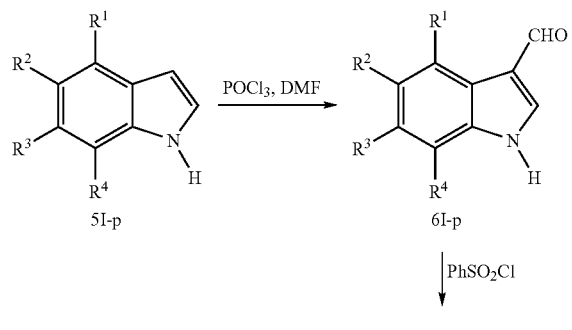

Aldehyde compounds 6 may be prepared by formylation of indoles 5 with phosphorus oxychloride in dimethyl formamide (DMF) (J. Chem. Soc. 1958, 3493). Benzenesulfonyl protection of indole 6 to 7 may be carried out by treatment with benzenesulfonyl chloride in the presence of a base (NaH or NaOH). The aldehyde 7 may be oxidized to the corresponding acid under appropriate oxidizing conditions such as with sodium chlorite (Acta Chem. Scand. 1973, 27, 888), then sequentially treated with trimethylsilyl diazomethane (TMSCHN$_2$) to give methyl ester preparations 1l-p. 1a-k may be synthesized from commercially available indole-3-carboxylic acid esters by reaction with benzenesulfonyl chloride in the presence of a base (e.g. sodium hydride or sodium hydroxide).

The synthetic route to N-alkylated compounds 11 is outlined in Scheme 3.

Scheme 3:

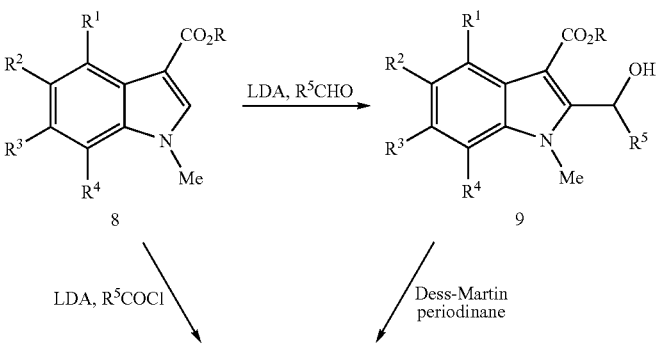

-continued

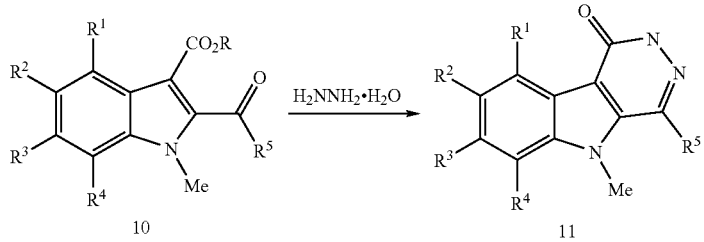

Alkylation of indole-3-carboxylate esters with alkyl halides and a base produces 8. Conversion of 8 to 9 or 10 may be achieved as described above for 2 and 3. 9 may be oxidized to 10 under the conditions described for 3. 10 may be converted to compounds 11 under the same conditions as described for Examples 4a-p.

The synthetic route to Examples 14 is outlined in Scheme 4.

Scheme 4:

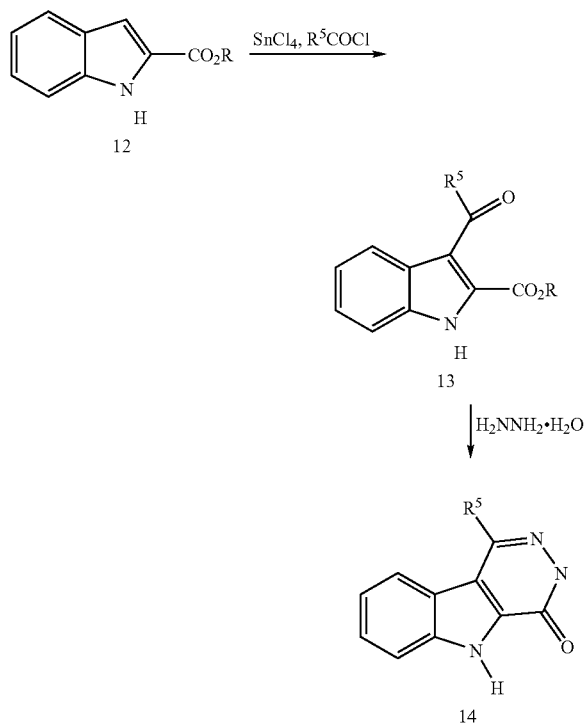

Compound 13 may be obtained from indole-2-carboxylate esters 12 by treatment with acid chlorides in the presence of an appropriate Lewis acid (e.g. tin tetrachloride). 13 may be converted to compounds 14 using the conditions as described for 4 above by treatment with hydrazine or hydrazine derivatives.

Aza compounds may be prepared using the general methods outlined in Scheme 1-4. As example, compounds of general structure 18 may be prepared as outlined in Scheme 5 using conditions described for Scheme 1.

Scheme 5:

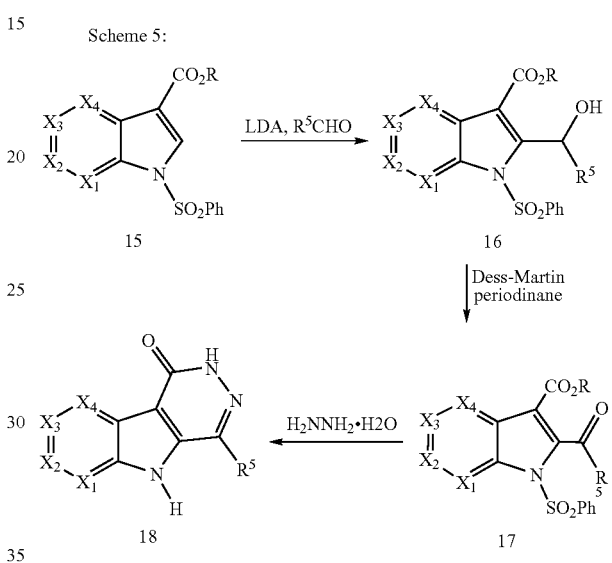

Aza derivative 15 (Comptes Rendus des Seances de l'Academie des Sciences, Serie C: Sciences Chimiques, 1967, 265, 1271; J. Heterocyclic Chem., 1968, 5, 461; J. Chem. Soc., Perkin Trans. 1, 1976, 13, 1361; Tetrahedron Lett. 2004, 45, 8087.; J. Chem. Soc. 1960, 131; Chem & Industry 1975, 5, 215. Diss. Abstr. Int. B 1974, 35, 1199), wherein $X_1$, $X_2$, $X_3$ and $X_4$ are selected from carbon and nitrogen, may be first treated with a base such as lithium diisopropylamide (LDA), and then with an aldehyde or acid chloride to give corresponding alcohols (16) or ketones (17). Treatment with hydrazine could provide 18.

Other features of the invention will become apparent in the course of the following descriptions of exemplary embodiments. These examples are given for illustration of the invention and are not intended to be limiting thereof.

EXAMPLES

Certain abbreviations used herein are defined as follows: "Bn" for benzyl, "DMF" for dimethyl formamide, "EtOAc" for ethyl acetate, "MeOH" for methanol, "EtOH" for ethanol, "THF" for tetrahydrofuran, "DMSOd$_6$" for deuterated dimethylsulfoxide, "rt" for room temperature, "d" for doublet, "dd" for doublet of doublets, "t" for triplet, "m" for multiplet, "J" for coupling constant, "br" for broad, "eq" or "equiv" for equivalents, "° C." for degrees Celsius, "mp" for melting point, "g" for gram or grams, "mg" for milligram or milligrams, "mL" for milliliter or milliliters, "H" for hydrogen or hydrogens, "hr" or "h" for hour or hours, "mmol" for millimoles, "min" or "m" for minute or minutes, "ppm" for parts per million, "MHz" for megahertz, "HPLC" for high performance liquid chromatography, "R$_t$" for retention time, "M"

for mass, "MS" for mass spectroscopy, and "NMR" for nuclear magnetic resonance spectroscopy.

Compounds

Compound 1a

1-Benzenesulfonyl-1H-indole-3-carboxylic acid methyl ester

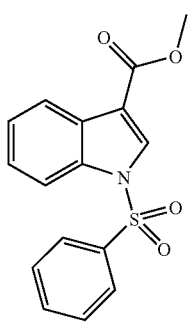

To a stirred solution of a suitable commercially available methyl indole-3-carboxylate (10 g, 57.1 mmol), tetrabutylammonium hydrogen sulfate (1.94 g, 5.71 mmol), and sodium hydroxide (22.8 g, 0.571 mmol) in a mixture solvent of $CH_2Cl_2$ (100 mL) and water (100 mL) at 0° C. was added benzenesulfonyl chloride (7.66 mL, 60.0 mmol). After 10 min at 0° C., the reaction was warmed to room temperature and stirred for an additional 4.5 h. The organic layer was separated and the aqueous layer was extracted with $CH_2Cl_2$ (50 mL). The combined organic layers were washed with brine, dried ($MgSO_4$), and concentrated in vacuo. The residue was triturated with diethyl ether and dried to give 16.8 g (92%) of compound 1a. $^1$H NMR (400 MHz, DMSO-$d_6$) δ 8.46 (s, 1H), 8.16 (m, 2H), 8.05 (m, 1H), 8.00 (m, 1H), 7.76 (m, 1H), 7.46 (m, 2H), 7.47-7.39 (m, 2H), 3.88 (s, 3H) ppm; MS (m/e) 316 (M+1).

The following compounds of formula 2 were prepared by the methods disclosed herein using the general method of Scheme 1, and methods known to one skilled in the art.

Compound 2a

1-Benzenesulfonyl-2-(hydroxyl-phenyl-methyl)-1H-indole-3-carboxylic acid methyl ester

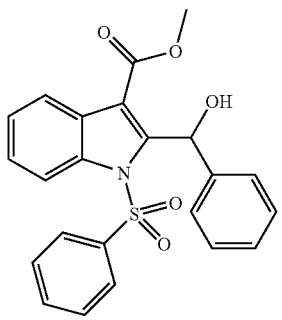

To a stirred solution of compound 1a (2.0 g, 6.34 mmol) in THF (30 mL) was added LDA (4.80 mL, 9.51 mmol)-78° C.

After 50 min, a solution of benzaldehyde (612 μL, 6.02 mmol) was added and continued to stir for 3 h. The reaction was quenched with brine (50 mL), and warmed to room temperature. The reaction mixture was extracted with EtOAc (50 mL×3). The combined organic extracts were washed with brine, dried ($Na_2SO_4$), and concentrated in vacuo. The residue was purified by flash column chromatography (Hexanes/EtOAc 6:1) gave 1.40 g (55%) of compound 2a. $^1$H NMR (400 MHz, DMSO-$d_6$) δ 8.13 (m, 1H), 7.83 (m, 3H), 7.69 (m, 1H), 7.54 (m, 2H), 7.45-7.24 (m, 7H), 6.94 (m, 1H), 6.33 (m, 1H), 3.76 (s, 3H) ppm; MS (m/e) 404 (M−OH).

Compounds 2b-2t were prepared using the procedure for compound 2a.

Compound 2b

1-Benzenesulfonyl-2-(hydroxyl-pyridin-2-yl-methyl)-1H-indole-3-carboxylic acid methyl ester

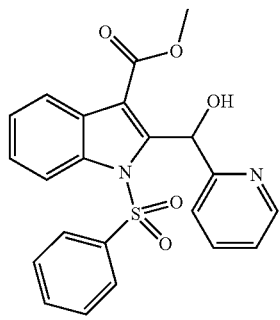

$^1$H NMR (400 MHz, DMSO-$d_6$) δ 8.35 (m, 1H), 8.11 (m, 2H), 8.04 (m, 1H), 7.93 (m, 1H), 7.84 (m, 1H), 7.69 (m, 2H), 7.58 (m, 2H), 7.40-7.34 (m, 2H), 7.24 (m, 2H), 6.56 (m, 1H), 3.70 (s, 3H) ppm; MS (m/e) 423 (M+H).

Compound 2c

1-Benzenesulfonyl-2-(hydroxyl-pyridin-3-yl-methyl)-1H-indole-3-carboxylic acid methyl ester

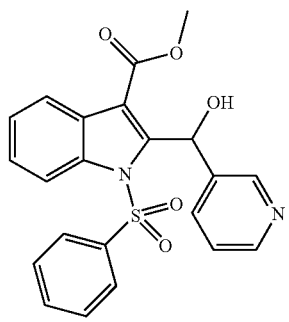

$^1$H NMR (400 MHz, DMSO-$d_6$) δ 8.54 (m, 1H), 8.46 (m, 1H), 8.14 (m, 1H), 7.94 (m, 2H), 7.85 (m, 1H), 7.71 (m, 2H), 7.57 (m, 2H), 7.46-7.32 (m, 3H), 7.00 (m, 1H), 6.59 (m, 1H), 3.79 (s, 3H) ppm; MS (m/e) 423 (M+H).

Compound 2d

1-Benzenesulfonyl-2-(hydroxyl-pyridin-4-yl-methyl)-1H-indole-3-carboxylic acid methyl ester

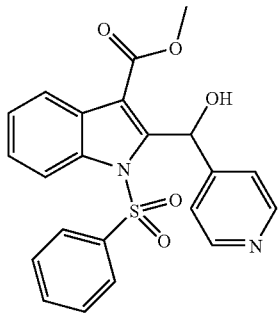

$^1$H NMR (400 MHz, DMSO-d$_6$) δ 8.49 (m, 2H), 8.15 (m, 1H), 8.02 (m, 2H), 7.94 (m, 1H), 7.72 (m, 1H), 7.59 (m, 2H), 7.47-7.37 (m, 2H), 7.29 (m, 2H), 7.07 (m, 1H), 6.64 (m, 1H), 3.78 (s, 3H) ppm; MS (m/e) 423 (M+H).

Compound 2e

1-Benzenesulfonyl-2-[hydroxyl-(5-methyl-furan-2-yl)-methyl]-1H-indole-3-carboxylic acid methyl ester

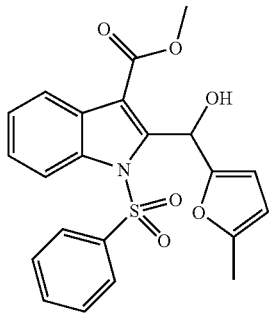

$^1$H NMR (400 MHz, DMSO-d$_6$) δ 8.13 (m, 1H0, 7.81 (m, 3H), 7.70 (m, 1H), 7.55 (m, 2H), 7.46-7.35 (m, 2H), 6.80 (m, 1H), 6.38 (m, 1H), 5.97 (m, 2H), 3.81 (s, 3H), 2.22 (s, 3H) ppm; MS (m/e) 408 (M–OH).

Compound 2f

1-Benzenesulfonyl-2-(hydroxy-thiazol-2-yl-methyl)-1H-indole-3-carboxylic acid methyl ester

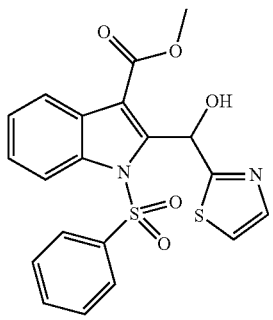

$^1$H NMR (400 MHz, DMSO-d$_6$) δ 8.12 (m, 2H), 8.06 (m, 1H), 7.94 (m, 1H), 7.72-7.57 (m, 5H0, 7.44-7.35 (m, 3H), 7.23 (m, 1H0, 3.76 (s, 3H) ppm; MS (m/e) 429 (M+H).

Compound 2g

1-Benzenesulfonyl-2-[hydroxy-(1-methyl-1H-imidazol-2-yl)-methyl]-1H-indole-3-carboxylic acid methyl ester

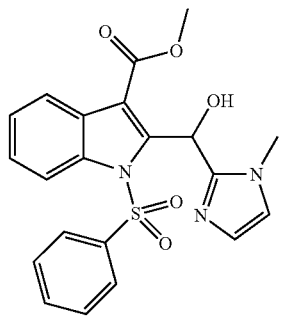

$^1$H NMR (400 MHz, DMSO-d$_6$) δ 8.00 (m, 1H), 7.90 (m, 2H), 7.67 (m, 1H), 7.55 (m, 2H), 7.41-7.34 (m, 2H), 7.14 (s, 1H), 7.01 (m, 1H), 6.69 (m, 2H), 3.93 (s, 1H), 3.83 (s, 3H), 3.80 (s, 3H) ppm; MS (m/e) 426 (M+H).

Compound 2h

1-Benzenesulfonyl-2-[hydroxy-(1-methyl-1H-benzoimidazol-2-yl)-methyl]-1H-indole-3-carboxylic acid methyl ester

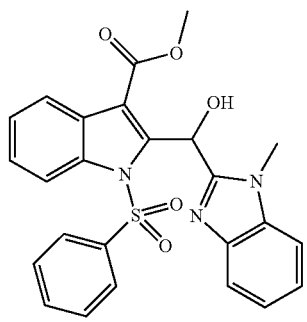

$^1$H NMR (400 MHz, DMSO-d$_6$) δ 8.10 (m, 2H), 7.94 (m, 2H), 7.67-7.51 (m, 4H), 7.38 (m, 2H), 7.34 (m, 1H), 7.26 (m, 1H), 7.17 (m, 2H), 6.98 (m, 1H), 4.03 (s, 3H), 3.81 (s, 3H) ppm; MS (m/e) 476 (M+H).

Compound 2i

1-Benzenesulfonyl-2-(biphenyl-4-yl-hydroxy-methyl)-1H-indole-3-carboxylic acid methyl ester

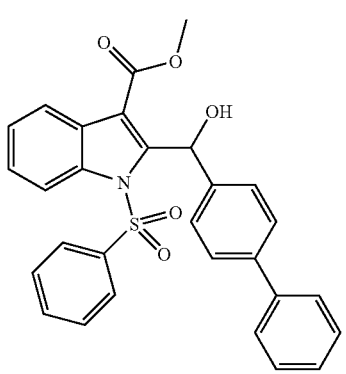

$^1$H NMR (400 MHz, DMSO-$d_6$) δ 8.15 (d, 1H), 7.86 (m, 2H), 7.69-7.35 (m, 161H), 6.98 (d, 1H), 3.79 (s, 3H) ppm; MS (m/e) 520 (M+Na).

Compound 2k

1-Benzenesulfonyl-2-(benzofuran-2-yl-hydroxy-methyl)-1H-indole-3-carboxylic acid methyl ester

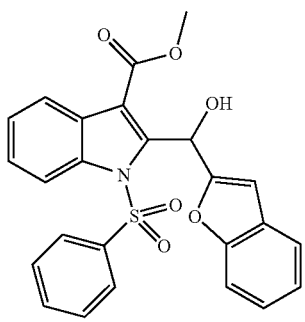

$^1$H NMR (400 MHz, DMSO-$d_6$) δ 8.15 (m, 1H), 7.95 (m, 2H), 7.86 (m, 1H), 7.68 (m, 1H), 7.58-7.45 (m, 5H), 7.40 (m, 1H), 7.28-7.20 (m, 2H), 7.10 (m, 1H), 6.74 (m, 1H), 6.63 (s, 1H), 3.77 (s, 3H) ppm; MS (m/e) 444 (M−OH).

Compound 2l

1-Benzenesulfonyl-2-(benzofuran-2-yl-hydroxymethyl)-5-methoxy-1H-indole-3-carboxylic acid methyl ester

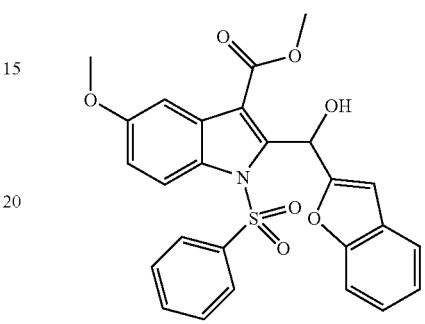

$^1$H NMR (400 MHz, DMSO-$d_6$) δ 8.06 (m, 1H), 7.91 (m, 2H), 7.67 (m, 1H), 7.57-7.49 (m, 4H), 7.31-7.20 (m, 3H), 7.07 (m, 2H), 6.71 (m, 1H), 6.62 (s, 1H), 3.80 (s, 3H), 3.76 (s, 3H) ppm; MS (m/e) 474 (M−OH).

Compound 2m

5-Benzenesulfonyl-6-(benzofuran-2-yl-hydroxymethyl)-5H-[1,3]dioxolo[4,5-f]indole-7-carboxylic acid methyl ester

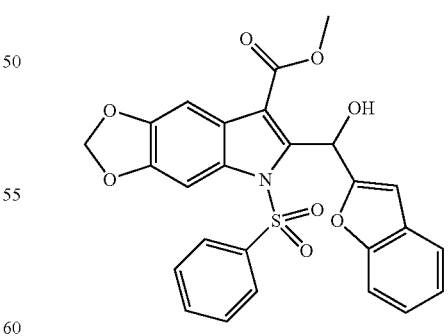

$^1$H NMR (400 MHz, DMSO-$d_6$) δ 7.96 (m, 2H), 7.72-7.48 (m, 6H), 7.30-7.21 (m, 3H), 7.05 (m, 1H), 7.62 (m, 2H), 6.11 (s, 2H), 3.75 (s, 3H) ppm; MS (m/e) 488 (M−OH).

Compound 2n

1-Benzenesulfonyl-2-(benzofuran-2-yl-hydroxy-methyl)-4-benzyloxy-1H-indole-3-carboxylic acid methyl ester

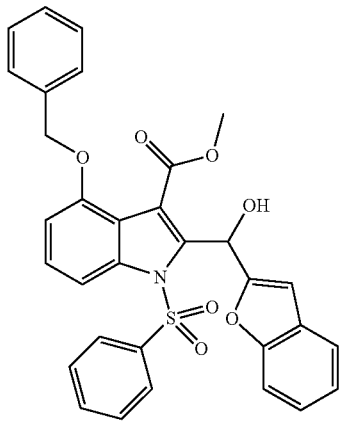

¹H NMR (400 MHz, DMSO-d₆) δ 7.81 (m, 2H), 7.65 (m, 2H), 7.57-7.20 (m, 15H), 6.97 (m, 1H), 6.77 (m, 1H), 6.67 (m, 2H), 6.48 (s, 2H), 5.12 (s, 2H) ppm; MS (m/e) 550 (M−OH), 590 (M+Na).

Compound 2o

1-Benzenesulfonyl-2-(benzofuran-2-yl-hydroxy-methyl)-5-benzyloxy-1H-indole-3-carboxylic acid methyl ester

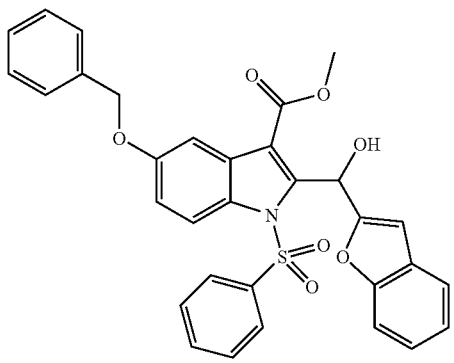

¹H NMR (400 MHz, DMSO-d₆) δ 8.06 (m, 1H), 7.91 (m, 2H), 7.67 (m, 1H), 7.57-7.07 (m, 14H), 6.71 (m, 1H), 6.61 (s, 1H), 5.15 (s, 2H), 3.76 (s, 3H) ppm; MS (m/e) 550 (M—OH).

Compound 2r

1-Benzenesulfonyl-2-[hydroxyl-(4-methoxy-phenyl)-methyl]-1H-indole-3-carboxylic acid methyl ester

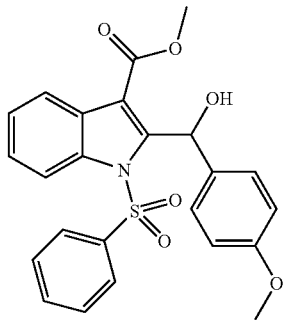

mp 72-73° C.; ¹H NMR (400 MHz, CDCl₃) δ 3.78 (s, 3H), 3.87 (s, 3H), 6.05 (d, J=8.5 Hz, 1H), 6.29 (d, J=7.5 Hz, 2H), 7.10 (d, J=8.0 Hz, 1H), 7.21 (d, J=8.0 Hz, 2H), 7.30 (m, 3H), 7.53 (t, J=8.0 Hz, 1H), 7.75 (d, J=8.0 Hz, 2H), 8.05 (d, J=8.0 Hz, 1H), 8.32 (d, J=8.0 Hz, 1H) ppm; MS (m/e) M+H 434.

Compound 2t

1-Benzenesulfonyl-2-[(4-benzyloxy-phenyl)-hydroxy-methyl]-6-methoxy-1H-indole-3-carboxylic acid methyl ester

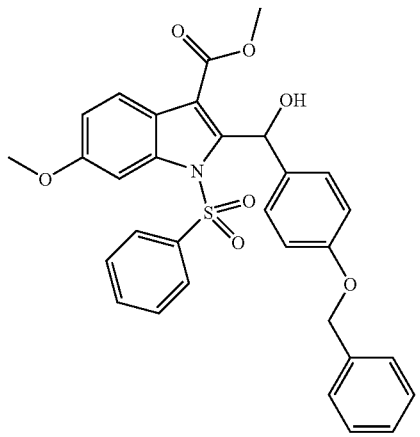

mp 64-66° C.; ¹H NMR (400 MHz, CDCl₃) δ 3.90 (s, 3H), 3.95 (s, 3H), 5.05 (s, 2H), 5.97 (d, J=8.5 Hz, 1H), 6.80 (d, J=7.5 Hz, 2H), 7.00 (d, J=6.0 Hz, 1H), 7.05 (d, J=8.0 Hz, 1H), 7.15 (d, J=8.0 Hz, 2H), 7.40 (m, 6H), 7.50 (t, J=8.0 Hz, 1H), 7.75 (d, J=8.0 Hz, 2H), 7.82 (s, 1H), 7.90 (d, J=8.0 Hz, 1H) ppm; MS (m/e) M+H 540 (557-17).

The following compounds of formula 3 were prepared by the methods disclosed herein using the general method of Scheme 1 and methods known to one skilled in the art.

Compound 3a

1-Benzenesulfonyl-2-benzoyl-1H-indole-3-carboxylic acid methyl ester

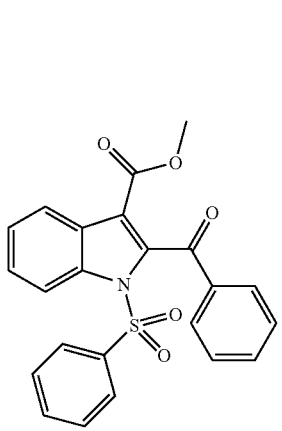

To a stirred solution of compound 2a (1.30 g, 3.08 mmol) in $CH_2Cl_2$ (30 mL) at room temperature was added Dess-Martin periodinane (1.96 g, 4.62 mmol). After 1.5 h, saturated aqueous solution of $NaHCO_3$ (80 mL) was added and stirred until the organic layer was clear. The reaction mixture was extracted with $CH_2Cl_2$ (100 mL and 50 mL). The combined extracts were washed with brine, dried ($MgSO_4$), concentrated in vacuo, and dried under vacuum to give 1.23 g (95%) of compound 3a. $^1H$ NMR (400 MHz, DMSO-$d_6$) δ 8.11-8.04 (m, 4H), 7.87 (m, 2H), 7.80-7.66 (m, 4H), 7.60-7.46 (m, 4H), 3.65 (s, 3H) ppm; MS (m/e) 420 (M+H).

Compounds 3b-3h, 3k-3p, 3r and 3t were prepared using the procedure for compound 3a.

Compound 3b

1-Benzenesulfonyl-2-(pyridine-2-carbonyl)-1H-indole-3-carboxylic acid methyl ester

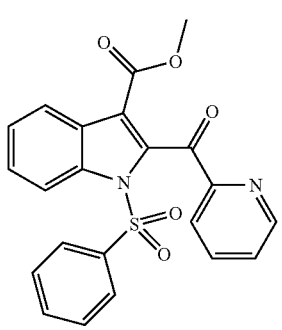

$^1H$ NMR (400 MHz, DMSO-$d_6$) δ 8.69 (m, 1H), 8.28 (m, 1H), 8.17-8.13 (m, 1H), 8.10-8.04 (m, 3H), 7.96 (m, 1H), 7.80-7.67 (m, 4H), 7.51-7.43 (m, 2H), 3.63 (s, 3H) ppm; MS (m/e) 421 (M+H).

Compound 3c

1-Benzenesulfonyl-2-(pyridine-3-carbonyl)-1H-indole-3-carboxylic acid methyl ester

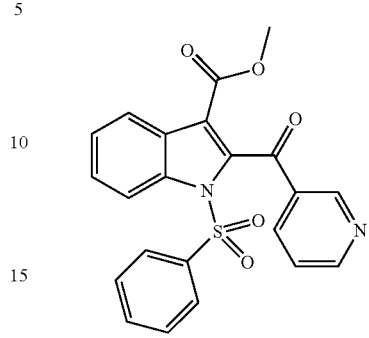

$^1H$ NMR (400 MHz, DMSO-$d_6$) δ 9.06 (m, 1H), 8.88 (m, 1H), 8.28 (m, 1H), 8.11-8.05 (m, 4H), 7.80 (m, 1H), 7.72-7.47 (m, 5H), 3.68 (s, 3H) ppm; MS (m/e) 421 (M+H).

Compound 3d

1-Benzenesulfonyl-2-(pyridine-4-carbonyl)-1H-indole-3-carboxylic acid methyl ester

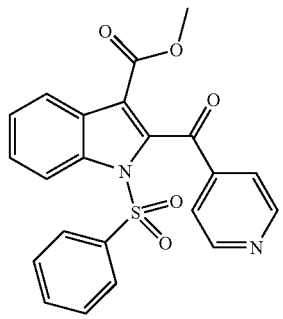

$^1H$ NMR (400 MHz, DMSO-$d_6$) δ 8.87 (m, 2H), 8.11-8.04 (m, 4H), 7.82-7.79 (m, 3H), 7.70 (m, 2H), 7.58-7.48 (m, 2H), 3.67 (s, 3H) ppm; MS (m/e) 421 (M+H).

Compound 3e

1-Benzenesulfonyl-2-(5-methyl-furan-2-carbonyl)-1H-indole-3-carboxylic acid methyl ester

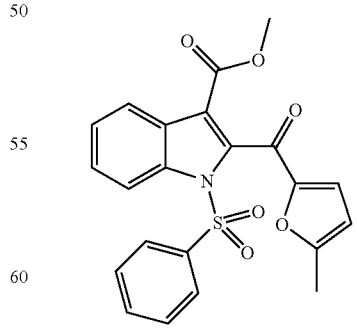

$^1H$ NMR (400 MHz, DMSO-$d_6$) δ 8.09-8.05 (m, 4H), 7.77 (m, 1H), 7.67 (m, 2H), 7.54-7.44 (m, 2H), 7.29 (s, 1H), 6.45 (m, 1H), 3.72 (s, 3H), 2.41 (s, 3H) ppm; MS (m/e) 424 (M+H).

Compound 3f

1-Benzenesulfonyl-2-(thiazole-2-carbonyl)-1H-indole-3-carboxylic acid methyl ester

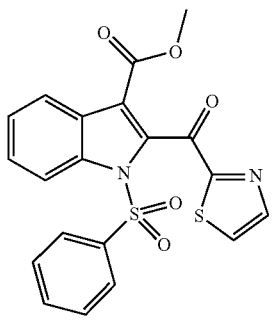

$^1$H NMR (400 MHz, DMSO-d$_6$) δ 8.39 (m, 1H), 8.16 (m, 1H), 8.04 (m, 4H), 7.78 (m, 1H), 7.68 (m, 2H), 7.55-7.46 (m, 2H), 3.69 (s, 3H) ppm; MS (m/e) 427 (M+H).

Compound 3g

1-Benzenesulfonyl-2-(1-methyl-1H-imidazole-2-carbonyl)-1H-indole-3-carboxylic acid methyl ester

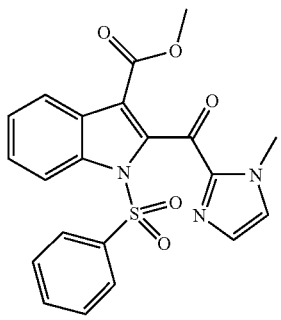

$^1$H NMR (400 MHz, DMSO-d$_6$) δ 8.12 (m, 2H), 8.04 (m, 1H), 7.95 (m, 1H), 7.76 (m, 1H), 7.65 (m, 3H), 7.50-7.42 (m, 2H), 7.15 (m, 1H), 4.13 (s, 3H), 3.70 (s, 3H) ppm; MS (m/e) 424 (M+H).

Compound 3h

1-Benzenesulfonyl-2-(1-methyl-1H-benzoimidazole-2-carbonyl)-1H-indole-3-carboxylic acid methyl ester

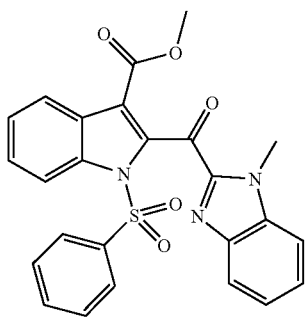

$^1$H NMR (400 MHz, DMSO-d$_6$) δ 8.18 (m, 2H0, 8.09-8.06 (m, 2H), 7.97 (m, 1H), 7.87-7.75 (m, 3H), 7.67 (m, 2H), 7.56 (m, 2H), 7.41-7.37 (m, 1H), 4.32 (s, 3H), 3.70 (s, 3H) ppm; MS (m/e) 474 (M+H).

Compound 3j

1-Benzenesulfonyl-2-(quinoxaline-2-carbonyl)-1H-indole-3-carboxylic acid methyl ester

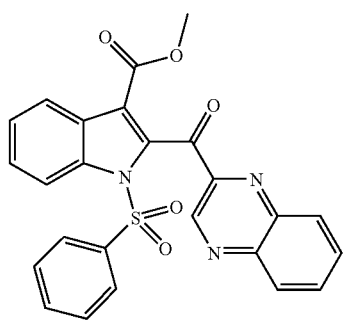

To a stirred solution of compound 1a (1.6 g, 5.19 mmol) in THF (20 mL) was added LDA (3.90 mL, 7.79 mmol)-78° C. After 40 min, a solution of quinoxaline-2-carbonyl chloride (1.0 g, 5.19 mmol) in (5 mL×2) was added and continued to stir for 5.5 h. The reaction was quenched with brine (50 mL), and warmed to room temperature. The reaction mixture was extracted with EtOAc (50 mL×3). The combined organic extracts were washed with brine, dried (Na$_2$SO$_4$), and concentrated in vacuo. The residue was purified by flash column chromatography (Hexanes/EtOAc 3:1) gave 641 mg (26%) of compound 3j. $^1$H NMR (400 MHz, DMSO-d$_6$) δ 9.77 (s, 1H), 8.30 (m, 1H), 8.15-8.07 (m, 5H), 8.00-7.95 (m, 2H), 7.79 (m, 1H), 7.70 (m, 2H), 7.57-7.48 (m, 2H), 3.64 (s, 3H) ppm; MS (m/e) 472 (M+H).

Compound 3k

1-Benzenesulfonyl-2-(benzofuran-2-carbonyl)-1H-indole-3-carboxylic acid methyl ester

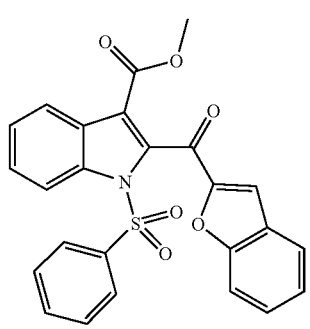

Compound 3l

1-Benzenesulfonyl-2-(benzofuran-2-carbonyl)-5-methoxy-1H-indole-3-carboxylic acid methyl ester

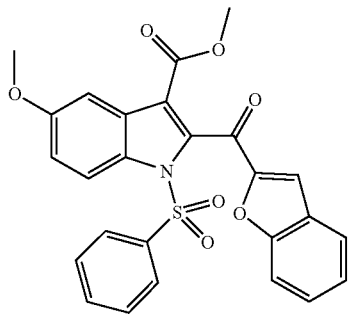

$^1$H NMR (400 MHz, DMSO-d$_6$) δ 8.04-7.98 (m, 3H), 7.86-7.77 (m, 4H), 7.69-7.59 (m, 4H), 7.41 (m, 1H), 7.17 (m, 1H), 3.83 (s, 3H), 3.69 (s, 3H) ppm; MS (m/e) 490 (M+H).

Compound 3m

5-Benzenesulfonyl-6-(benzofuran-2-carbonyl)-5H-[1,3]dioxolo[4,5-f]indole-7-carboxylic acid methyl ester

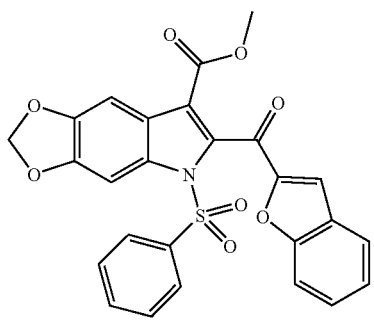

$^1$H NMR (400 MHz, DMSO-d$_6$) δ 8.09 (m, 2H), 7.84-7.58 (m, 8H), 7.43 (m, 2H), 6.16 (s, 2H), 3.67 (s, 3H) ppm; MS (m/e) 503 (M$^+$), 504 (M+H).

$^1$H NMR (400 MHz, DMSO-d$_6$) δ 8.13-8.06 (m, 4H), 7.89 (s, 1H), 7.85-7.78 (m, 3H), 7.68 (m, 2H), 7.63-7.48 (m, 3H), 7.41 (m, 1H), 3.71 (s, 3H) ppm; MS (m/e) 460 (M+H).

Compound 3n

1-Benzenesulfonyl-2-(benzofuran-2-carbonyl)-4-benzyloxy-1H-indole-3-carboxylic acid methyl ester

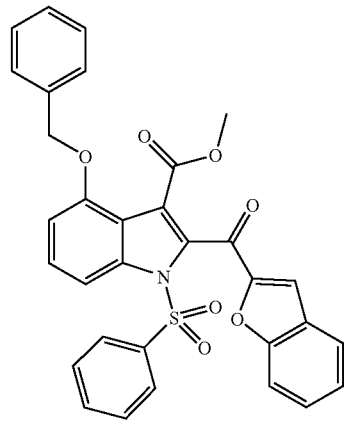

$^1$H NMR (400 MHz, DMSO-d$_6$) δ 8.02 (m, 3H), 7.86-7.77 (m, 4H), 7.69-7.59 (m, 4H), 7.49-7.33 (m, 6H), 7.25 (m, 1H), 5.18 (s, 2H), 3.69 (s, 3H) ppm; MS (m/e) 566 (M+H).

Compound 3o

1-Benzenesulfonyl-2-(benzofuran-2-carbonyl)-5-benzyloxy-1H-indole-3-carboxylic acid methyl ester

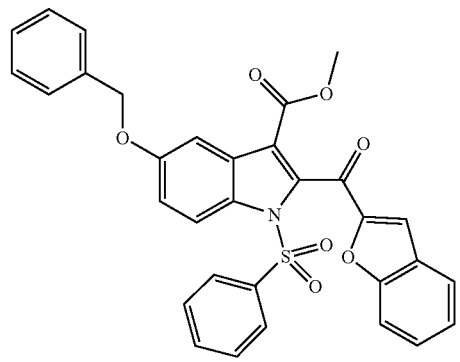

$^1$H NMR (400 MHz, DMSO-d$_6$) δ 8.05-7.98 (m, 3H), 7.86-7.77 (m, 4H), 7.69-7.59 (m, 4H), 7.48 (m, 2H), 7.43-7.38 (m, 3H), 7.33 (m, 1H), 7.25 (m, 1H), 5.18 (s, 2H), 3.69 (s, 3H) ppm; MS (m/e) 566 (M+H).

Compound 3p

1-Benzenesulfonyl-2-(benzofuran-2-carbonyl)-6-benzyloxy-1H-indole-3-carboxylic acid methyl ester

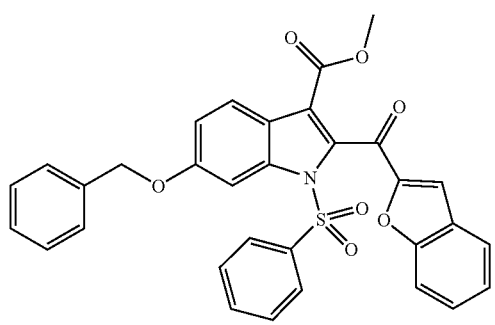

$^1$H NMR (400 MHz, DMSO-d$_6$) δ 7.98-7.37 (m, 17H), 7.22 (m, 1H), 5.29 (s, 2H), 3.68 (s, 3H) ppm; MS (m/e) 566 (M+H).

Compound 3r

1-Benzenesulfonyl-2-(4-methoxy-benzoyl)-1H-indole-3-carboxylic acid methyl ester

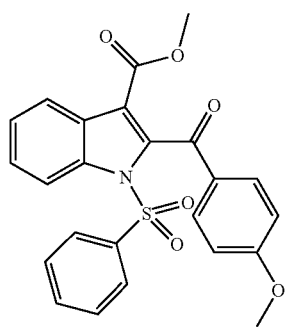

$^1$H NMR (400 MHz, CDCl$_3$) δ 3.69 (s, 3H), 3.89 (s, 3H), 6.97 (d, J=8.0 Hz, 2H), 7.40 (m, 2H), 7.52 (d, J=8.0 Hz, 2H), 7.59 (t, J=8.0 Hz, 1H), 7.90 (d, J=8.0 Hz, 2H), 8.00 (d, J=8.0 Hz, 1H), 8.10 (d, J=8.0 Hz, 2H), 8.26 (d, J=8.0 Hz, 1H) ppm; MS (m/e) M+H 450.

Compound 3t

1-Benzenesulfonyl-2-(4-benzyloxy-benzoyl)-6-methoxy-1H-indole-3-carboxylic acid methyl ester

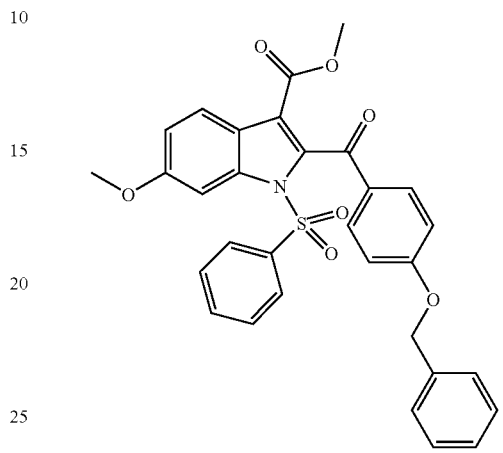

$^1$H NMR (400 MHz, CDCl$_3$) δ 3.65 (s, 3H), 3.90 (s, 3H), 5.15 (s, 2H), 7.05 (m, 3H), 7.40 (m, 5H), 7.52 (m, 2H), 7.58 (m, 2H), 7.92 (d, J=8.0 Hz, 2H), 8.00 (d, J=8.0 Hz, 1H), 8.07 (d, J=8.0 Hz, 2H) ppm; M+H 556.

The following compounds of formula 6 were prepared by the methods disclosed herein using the general method of Scheme 2 and methods known to one skilled in the art.

Compound 6o

5-Benzyloxy-1H-indole-3-carbaldehyde

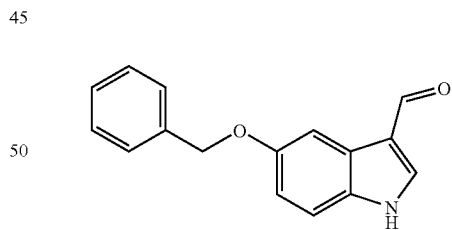

To a stirred solution of phosphorus oxychloride (2.29 mL, 24.6 mmol) in DMF (15 mL), was added a solution of 5-benzyloxyindole (5.00 g, 22.4 mmol) in DMF (20 mL) at room temperature. After 30 min, the reaction mixture was poured into ice-water (50 mL). To this mixture was added solid NaOH (4.80 g, 0.112 mol) and water (50 mL). The precipitate was collected, washed with EtOH, and dried to give 4.67 g (83%) of compound 6o. $^1$H NMR (400 MHz, DMSO-d$_6$) δ 12.01 (s, 1H), 9.89 (s, 1H), 8.21 (s, 1H), 7.68 (m, 1H), 7.49-7.30 (m, 6H), 6.97 (m, 1H), 5.12 (s, 2H) ppm; MS (m/e) 251 (M), 252 (M+H).

Compounds 6l, 6m and 6p were prepared using the procedure for compound 6o.

Compound 6l

5-Methoxy-1H-indole-3-carbaldehyde

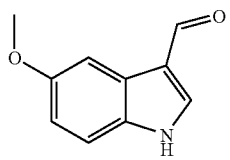

$^1$H NMR (400 MHz, DMSO-d$_6$) δ 12.00 (s, 1H), 9.89 (s, 1H), 8.20 (m, 1H), 7.58 (m, 1H), 7.40 (m, 1H), 6.88 (m, 1H), 3.78 (s, 3H) ppm; MS (m/e) 175 (M$^+$), 176 (M+H).

Compound 6m

5H-[1,3]Dioxolo[4,5-f]indole-7-carbaldehyde

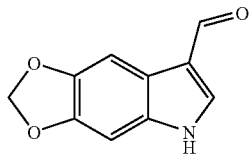

$^1$H NMR (400 MHz, DMSO-d$_6$) δ 11.91 (s, 1H), 9.83 (s, 1H), 8.07 (m, 1H), 7.46 (s, 1H), 7.02 (s, 1H), 6.00 (s, 2H) ppm; MS (m/e) 190 (M+H).

Compound 6p

6-Benzyloxy-1H-indole-3-carbaldehyde

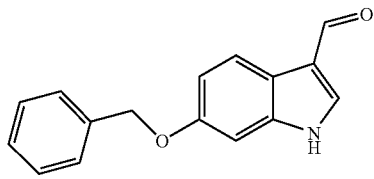

$^1$H NMR (400 MHz, DMSO-d$_6$) δ 11.92 (s, 1H), 9.86 (s, 1H), 8.14 (m, 1H), 7.94 (m, 1H), 7.48-7.32 (m, 5H), 7.06 (m, 1H), 6.95 (m, 1H), 5.14 (s, 2H) ppm; MS (m/e) 252 (M+H).

The following compounds of formula 7 were prepared by the methods disclosed herein using the general method of Scheme 2 and methods known to one skilled in the art.

Compound 7o

1-Benzenesulfonyl-5-benzyloxy-1H-indole-3-carbaldehyde

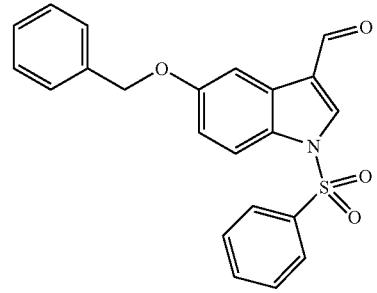

To a stirred mixture of compound 6o (3.0 g, 11.9 mmol), NaOH (4.76 g, 119 mmol), and tetrabutylammonium hydrogen sulfate (808 mg, 2.38 mmol) in a mixture of CH$_2$Cl$_2$ (30 mL) and H$_2$O (30 mL) was added benzenesulfonyl chloride (1.60 mL, 12.5 mmol) at 0° C. The reaction was warmed to room temperature and THF (20 mL) was added. After stirring for 1.5 h, the mixture was extracted with CH$_2$Cl$_2$ (50 mL×3). The combined organic extracts were washed with brine, dried (MgSO$_4$), filtered, concentrated in vacuo, and dried to give 4.92 g of compound 7o. $^1$H NMR (400 MHz, DMSO-d$_6$) δ 10.05 (s, 1H), 8.84 (s, 1H), 8.10 (m, 2H), 7.87 (m, 1H), 7.77 (m, 1H), 7.66 (m, 3H), 7.46-7.30 (m, 5H), 7.14 (m, 1H), 5.13 (s, 2H) ppm; MS (m/e) 391 (M$^+$), 392 (M+H).

Compounds 7l, 7m, 7n and 7p were prepared using the procedure for compound 7o.

Compound 7l

1-Benzenesulfonyl-5-methoxy-1H-indole-3-carbaldehyde

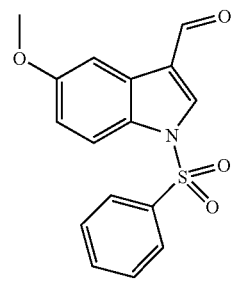

$^1$H NMR (400 MHz, DMSO-d$_6$) δ 10.06 (s, 1H), 8.84 (s, 1H), 8.10 (m, 2H), 7.87 (m, 1H), 7.77 (m, 1H), 7.65 (m, 2H), 7.58 (m, 1H), 7.06 (m, 1H), 3.78 (s, 3H) ppm; MS (m/e) 315 (M$^+$), 316 (M+H).

Compound 7m

5-Benzenesulfonyl-5H-[1,3]dioxolo[4,5-f]indole-7-carbaldehyde

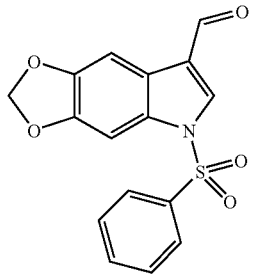

7m: $^1$H NMR (400 MHz, DMSO-d$_6$) δ 9.99 (s, 1H), 8.71 (s, 1H), 8.13 (m, 2H), 7.78 (m, 1H), 7.67 (m, 2H), 7.47 (m, 2H), 6.09 (s, 2H) ppm; MS (m/e) 329 (M$^+$), 330 (M+H).

Compound 7n

1-Benzenesulfonyl-4-benzyloxy-1H-indole-3-carbaldehyde

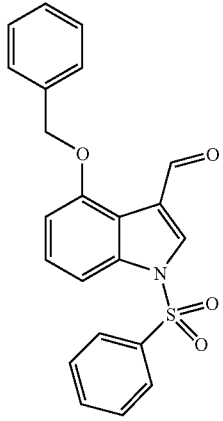

$^1$H NMR (400 MHz, DMSO-d$_6$) δ 10.35 (s, 1H), 8.40 (s, 1H), 8.15 (m, 2H), 7.76 (m, 1H), 7.66-7.58 (m, 3H), 7.50 (m, 2H0, 7.41-7.32 (m, 4H), 7.08 (m, 1H), 5.28 (s, 2H) ppm; MS (m/e) 392 (M+H).

Compound 7p

1-Benzenesulfonyl-6-benzyloxy-1H-indole-3-carbaldehyde

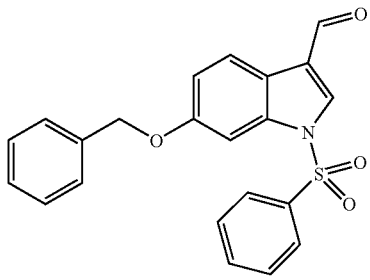

$^1$H NMR (400 MHz, DMSO-d$_6$) δ 10.01 (s, 1H), 8.74 (s, 1H), 7.98 (m, 3H), 7.75 (m, 1H), 7.61 (m, 2H), 7.50-7.37 (m, 6H), 7.12 (m, 1H), 5.23 (s, 2H) ppm; MS (m/e) 414 (M+Na).

The following compounds of formula 1 were prepared by the methods disclosed herein using the general method of Scheme 2 and methods known to one skilled in the art.

Compound 1o

1-Benzenesulfonyl-5-benzyloxy-1H-indole-3-carboxylic acid methyl ester

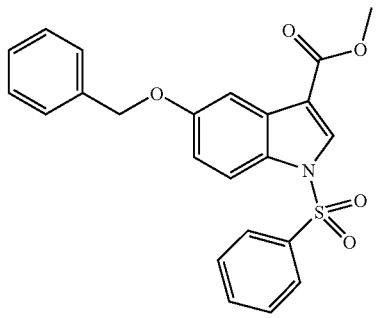

To a stirred solution of compound 7o (6.41 g, 16.4 mmol), tetrabutylammonium hydrogen sulfate (1.11 g, 3.28 mmol), 2-methyl-2-butene (25 mL, 0.298 mol) in CH$_2$Cl$_2$ (70 mL), was added a solution of sodium chlorite (13.9 g, 0.123 mol) and sodium phosphate, monobasic, monohydrate (17.0 g, 0.123 mol) in water (70 mL) slowly. After stirred for 1.5 h, the reaction was added with water (50 mL) and acidified to pH 2. The organic layer was separated, and the aqueous layer was extracted with ethyl acetate (100 mL×3). The combined organic layers were washed with brine, and concentrated in vacuo. To this residue was added CH$_2$Cl$_2$ (100 mL) and stirred at room temperature. Trimethylsilyldiazomethane (8.6 mL, 17.2 mmol) was added slowly and stirred for 30 min. The reaction was quenched with a few drops of acetic acid, dried (MgSO$_4$), and concentrated in vacuo. The residue was purified by flash column chromatography (hexanes/EtOAc 5:1 then 3:1) to give 4.12 g (60%) of compound 1o. $^1$H NMR (400 MHz, DMSO-d$_6$) δ 8.39 (s, 1H), 8.12 (m, 2H), 7.88 (m, 1H), 7.75 (m, 1H), 7.65-7.57 (m, 3H), 7.46-7.32 (m, 5H), 7.13 (m, 1H), 5.13 (s, 2H), 3.85 (s, 3H) ppm; MS (m/e) 421 (M$^+$), 422 (M+H).

Compounds 1l, 1m, 1n, and 1p were prepared using the procedure for compound 1o.

Compound 1l

1-Benzenesulfonyl-5-methoxy-1H-indole-3-carboxylic acid methyl ester

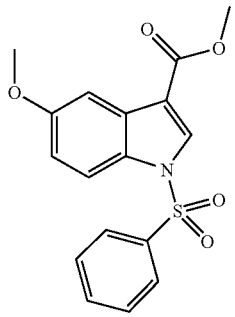

¹H NMR (400 MHz, DMSO-d₆) δ 8.39 (s, 1H), 8.11 (m, 2H), 7.87 (m, 1H), 7.75 (m, 1H), 7.63 (m, 2H), 7.48 (m, 1H), 7.05 (m, 1H), 3.86 (s, 3H), 3.78 (s, 3H) ppm; MS (m/e) 346 (M+H).

Compound 1m

5-Benzenesulfonyl-5H-[1,3]dioxolo[4,5-f]indole-7-carboxylic acid methyl ester

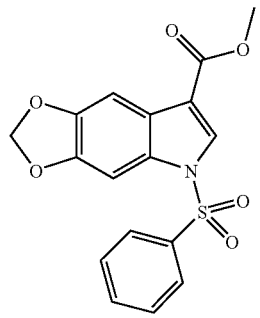

¹H NMR (400 MHz, DMSO-d₆) δ 8.27 (s, 1H), 8.15 (m, 2H), 7.65 (m, 1H), 7.64 (m, 2H), 7.49 (s, 1H), 7.39 (s, 1H), 6.09 (s, 2H), 3.84 (s, 3H) ppm; MS (m/e) 359 (M+), 360 (M+H).

Compound 1n

1-Benzenesulfonyl-4-benzyloxy-1H-indole-3-carboxylic acid methyl ester

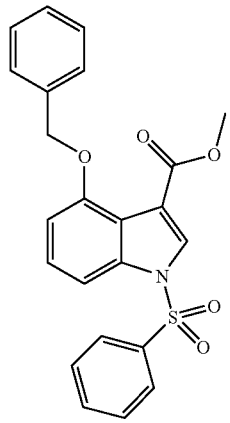

¹H NMR (400 MHz, DMSO-d₆) δ 8.21 (s, 1H), 8.09 (m, 2H), 7.75 (m, 1H), 7.64 (m, 2H), 7.56 (m, 1H), 7.49 (m, 2H), 7.40-7.29 (m, 4H), 6.98 (m, 1H), 5.17 (s, 2H), 3.63 (s, 3H) ppm.

Compound 1p

1-Benzenesulfonyl-6-benzyloxy-1H-indole-3-carboxylic acid methyl ester

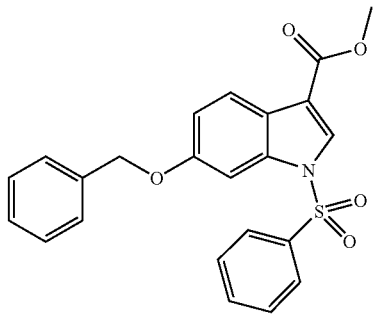

¹H NMR (400 MHz, DMSO-d₆) δ 8.30 (m, 1H), 8.02 (m, 2H), 7.90 (m, 1H), 7.73 (m, 1H), 7.59 (m, 2H), 7.51-7.36 (m, 6H), 7.12 (m, 1H), 5.24 (s, 2H), 3.84 (s, 3H) ppm; MS (m/e) 444 (M+Na).

The following compound of formula 9 was prepared by methods disclosed herein using the general method of Scheme 3 and methods known to one skilled in the art.

Compound 9a 2-(Benzofuran-2-yl-hydroxy-methyl)-1-methyl-1H-indole-3-carboxylic acid methyl ester

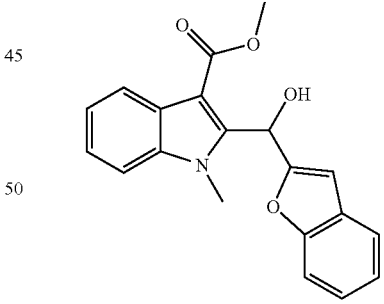

The procedure was the same as was described for the synthesis of compound 2a.

¹H NMR (400 MHz, DMSO-d₆) δ 8.05 (m, 1H), 7.60-7.49 (m, 3H), 7.36-7.19 (m, 5H), 6.89 (m, 1H), 6.77 (s, 1H), 3.91 (s, 3H), 3.88 (s, 3H) ppm; MS (m/e) 318 (M−OH), 358 (M+Na).

The following compounds of formula 10 were prepared by the methods disclosed herein using the general method of Scheme 3 and methods known to one skilled in the art.

Compound 10a 2-(Benzo[i]ran-2-carbonyl)-1-methyl-1H-indole-3-carboxylic acid methyl ester

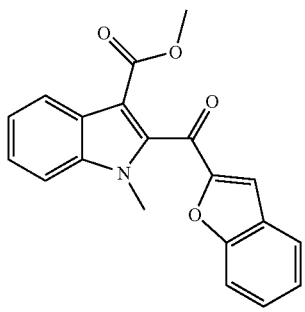

The procedure was the same as described for the synthesis of compound 3a. $^1$H NMR (400 MHz, DMSO-$d_6$) δ 8.09 (m, 1H), 7.82-7.70 (m, 4H), 7.59 (m, 1H), 7.46-7.35 (m, 3H), 3.80 (s, 3H), 3.58 (s, 3H) ppm; MS (m/z) 334 (M+H).

Compound 10b 2-(Benzo[b]thiophene-2-carbonyl)-1-methyl-1H-indole-3-carboxylic acid methyl ester

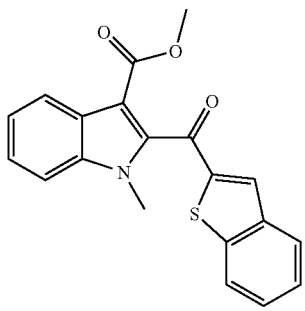

To a stirred solution of methyl 1-methyl-indole-3-carboxylate (1.0 g, 3.54 mmol) in THF (20 mL) was added LDA (2.67 mL, 5.31 mmol) at −78° C. and stirred for 50 min. A solution of benzo[b]thiophene-2-carbonyl chloride (696 mg, 3.54 mmol) in THF (10 mL) was added. After stirring for 4.5 h, the reaction was quenched with brine and warmed to room temperature. The reaction mixture was extracted with EtOAc (50 mL×3). The combined organic extracts were washed with brine, dried (MgSO$_4$), and concentrated in vacuo. The residue was purified by flash column chromatography (Hexanes/EtOAc 3:1) gave 591 mg (48%) of compound 10b. $^1$H NMR (400 MHz, DMSO-$d_6$) δ 8.11 (m, 2H), 7.99 (m, 1H), 7.94 (s, 1H), 7.73 (m, 1H), 7.58 (m, 1H), 7.48-7.35 (m, 3H), 3.77 (s, 3H), 3.60 (s, 3H) ppm; MS (m/e) 350 (M+H).

The following compounds of formula 13 were prepared by the methods disclosed herein using the general method of Scheme 4 and methods known to one skilled in the art.

Compound 13a 3-(4-Methyl-benzoyl)-1H-indole-2-carboxylic acid ethyl ester

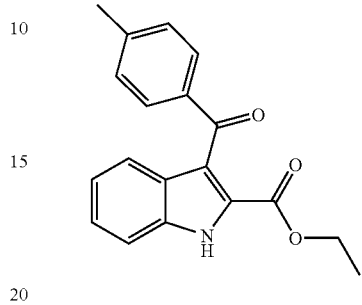

To a stirred solution of indole-2-carboxylic acid ethyl ester (1.0 g, 5.29 mmol) in CH$_2$Cl$_2$ (10 mL) was added tin (IV) chloride (6.35 mL, 6.35 mmol) at 0° C. The reaction was stirred at room temperature for 35 min. A solution of 4-methyl-benzoylchloride (700 mg, 5.29 mmol) in CH$_3$NO$_2$ (7.5 mL) was added and stirred for 2 h. The reaction was poured into an ice-water (30 mL) and warmed to room temperature. The reaction mixture was extracted with CH$_2$Cl$_2$ (50 mL×3). The combined organic extracts were washed with brine, dried (MgSO$_4$), and concentrated in vacuo. The residue was purified by flash column chromatography (Hexanes/EtOAc 4:1) to give 1.38 g (85%) of compound 13a. $^1$H NMR (400 MHz, DMSO-$d_6$) δ 12.46 (s, 1H), 7.64 (m, 2H), 7.55 (m, 2H), 7.36-7.29 (m, 3H), 7.15 (m, 1H), 3.98 (m, 2H), 2.37 (s, 3H0, 0.86 (m, 3H) ppm; MS (m/e) 308 (M+H).

Compounds 13c and 13d were prepared using the procedure for compound 13a.

Compound 13c 3-(Naphthalene-2-carbonyl)-1H-indole-2-carboxylic acid ethyl ester

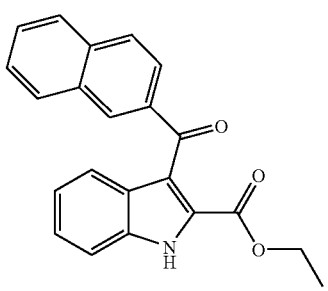

$^1$H NMR (400 MHz, DMSO-$d_6$) δ 12.56 (s, 1H), 8.27 (s, 1H), 8.05-8.00 (m, 3H), 7.93 (m, 1H), 7.67-7.55 (m, 4H), 7.38 (m, 1H), 7.19 (m, 1H), 3.86 (m, 2H), 0.68 (m, 3H) ppm; MS (m/e) 344 (M+H).

Compound 13d 3-(4-Methoxy-benzoyl)-1H-indole-2-carboxylic acid ethyl ester

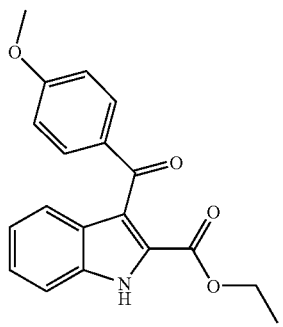

$^1$H NMR (400 MHz, DMSO-d$_6$) δ 12.42 (s, 1H), 7.72 (m, 2H), 7.57-7.49 (m, 2H), 7.37-7.32 (m, 1H), 7.17-7.13 (m, 1H), 7.02 (m, 2H), 4.05-4.00 (m, 2H), 0.92-0.88 (m, 3H) ppm; MS (m/e) 324 (M+1).

The following compounds of formula 4 were prepared by the methods disclosed herein using the general method of Scheme 1 and methods known to one skilled in the art.

Compound 4a

4-Phenyl-2,5-dihydro-pyridazino[4,5-b]indol-1-one

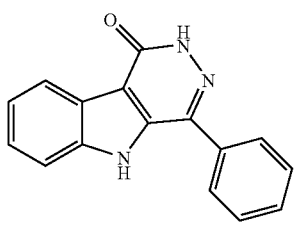

A mixture of compound 3a (268 mg, 0.639 mmol), H$_2$NNH$_2$·H$_2$O (62 μL, 1.28 mmol), and EtOH (8 mL) in a 50 mL flask was heated to reflux over night. After cooled to room temperature, the precipitate was collected by filtration, raised with EtOH, and dried to give 107 mg (64%) of compound 4a. $^1$H NMR (400 MHz, DMSO-d$_6$) δ 12.84 (s, 1H), 12.09 (s, 1H), 8.24 (m, 1H), 7.84 (m, 2H), 7.69 (m, 1H), 7.64-7.55 (m, 3H), 7.49 (m, 1H), 7.35 (m, 1H) ppm; MS (m/z) 262 (M+H).

Examples 4b-4p and 4r were prepared using the procedure for compound 4a.

Example 4b

4-Pyridin-2-yl-2,5-dihydro-pyridazino[4,5-b]indol-1-one

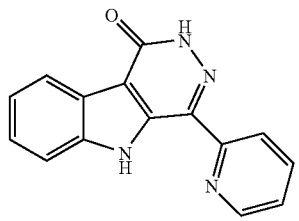

$^1$H NMR (400 MHz, DMSO-d$_6$) δ 13.01 (s, 1H), 12.31 (s, 1H), 8.85 (m, 1H), 8.24 (m, 2H), 8.03 (m, 1H), 7.92 (m, 1H), 7.57-7.50 (m, 2H), 7.35 (m, 1H) ppm; MS (m/z) 263 (M+H).

Example 4c

4-Pyridin-3-yl-2,5-dihydro-pyridazino[4,5-b]indol-1-one

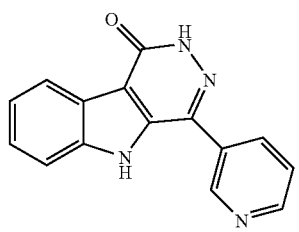

$^1$H NMR (400 MHz, DMSO-d$_6$) δ 12.96 (s, 1H), 12.27 (s, 1H), 9.03 (m, 1H), 8.76 (m, 1H), 8.24 (m, 2H), 7.69-7.62 (m, 2H), 7.51 (m, 1H), 7.36 (m, 1H) ppm; MS (m/e) 263 (M+H).

Example 4d

4-Pyridin-4-yl-2,5-dihydro-pyridazino[4,5-b]indol-1-one

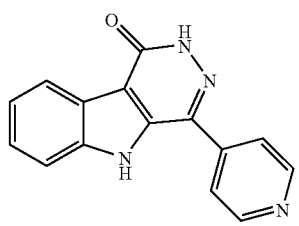

$^1$H NMR (400 MHz, DMSO-d$_6$) δ 13.05 (s, 1H), 12.24 (s, 1H), 8.81 (m, 2H), 8.24 (m, 1H), 7.85 (m, 2H), 7.70 (m, 1H), 7.52 (m, 1H), 7.36 (m, 1H) ppm; MS (m/e) 263 (M+H).

Example 4e 4-(5-Methyl-furan-2-yl)-2,5-dihydro-pyridazino[4,5-b]indol-1-one

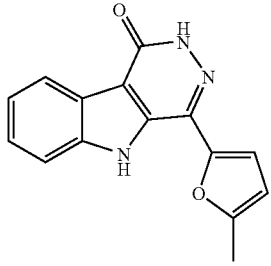

¹H NMR (400 MHz, DMSO-d₆) δ 12.77 (s, 1H), 11.88 (s, 1H), 8.23 (m, 1H), 7.80 (m, 1H0, 7.53 (m, 1H), 7.36 (m, 1H), 7.08 (m, 1H), 6.39 (m, 1H), 3.40 (s, 3H) ppm; MS (m/e) 266 (M+H).

Example 4f

4-Thiazo-2-yl-2,5-dihydro-pyridazino[4,5-b]indol-1-one

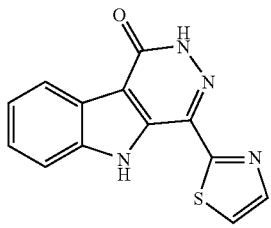

¹H NMR (400 MHz, DMSO-d₆) δ 13.07 (s, 1H), 12.20 (s, 1H), 8.22 (m, 1H), 8.15 (m, 1H), 7.95 (m, 2H), 7.52 (m, 1H), 7.36 (m, 1H) ppm; MS (m/e) 269 (M+H).

Example 4g 4-(1-Methyl-1H-imidazol-2-yl)-2,5-dihydro-pyridazino[4,5-b]indol-1-one

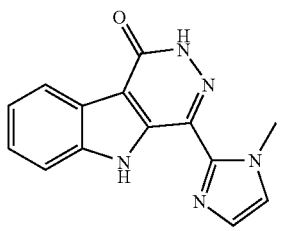

¹H NMR (400 MHz, DMSO-d₆) δ 12.86 (s, 1H), 12.05 (s, 1H), 8.20 (m, 1H), 7.94 (m, 1H), 7.48 (m, 2H), 7.33 (m, 1H), 7.25 (m, 1H), 4.04 (s, 3H) ppm; MS (m/e) 266 (M+H).

Example 4h 4-(1-Methyl-1H-benzoimidazol-2-yl)-2,5-dihydro-pyridazino[4,5-b]indol-1-one

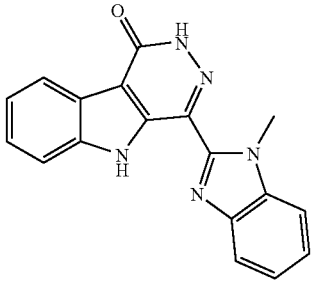

¹H NMR (400 MHz, DMSO-d₆) δ 13.17 (s, 1H), 12.19 (s, 1H), 8.24 (m, 1H), 7.99 (m, 1H), 7.91 (m, 1H), 7.73 (m, 1H), 7.53 (m, 1H), 7.44-7.35 (m, 3H), 4.22 (s, 3H) ppm; MS (m/e) 316 (M+H).

Example 4i

4-Biphenyl-4-yl-2,5-dihydro-pyridazino[4,5-b]indol-1-one

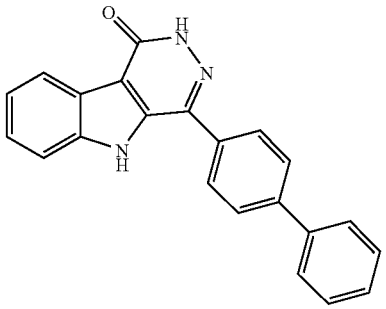

¹H NMR (400 MHz, DMSO-d₆) δ 12.87 (s, 1H), 12.17 (s, 1H), 8.25 (m, 1H), 7.93 (m, 4H), 7.79 (m, 2H), 7.70 (m, 1H), 7.52 (m, 3H), 7.43 (m, 1H), 7.35 (m, 1H) ppm; MS (m/e) 338 (M+H).

Example 4j

4-Quinoxalin-2-yl-2,5-dihydro-pyridazino[4,5-b]indol-1-one

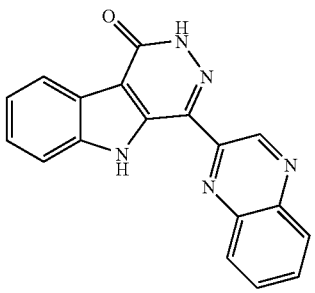

$^1$H NMR (400 MHz, DMSO-d$_6$) δ 13.34 (s, 1H), 12.29 (s, 1H), 9.74 (s, 1H), 8.70 (m, 1H), 8.28 (m, 1H), 8.18 (m, 1H), 8.03-7.92 (m, 3H), 7.59 (m, 1H), 7.40 (m, 1H) ppm; MS (m/e) 314 (M+H).

Example 4k

4-Benzofuran-2-yl-2,5-dihydro-pyridazino[4,5-b]indol-1-one

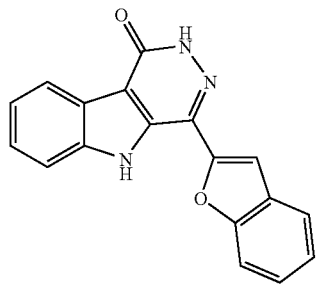

$^1$H NMR (400 MHz, DMSO-d$_6$) δ 13.08 (s, 1H), 12.23 (s, 1H), 8.26 (m, 1H), 7.83 (m, 2H), 7.64 (s, 1H), 7.56 (m, 1H), 7.46 (m, 1H), 7.38 (m, 3H) ppm; MS (m/e) 302 (M+H).

Example 4l

4-Benzofuran-2-yl-8-methoxy-2,5-dihydro-pyridazino[4,5-b]indol-1-one

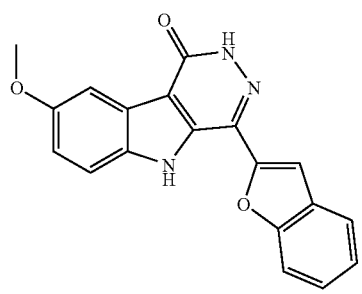

$^1$H NMR (400 MHz, DMSO-d$_6$) δ 13.01 (s, 1H), 12.12 (s, 1H), 7.81-7.68 (m, 4H), 7.62 (s, 1H), 7.46 (m, 1H), 7.36 (m, 1H), 7.20 (m, 1H), 3.87 (s, 3H) ppm; MS (m/e) 332 (M+H).

Example 4m

8-Benzofuran-2-yl-6,9-dihydro-1,3-dioxa-6,7,9-triaza-cyclopenta[b]fluoren-5-one

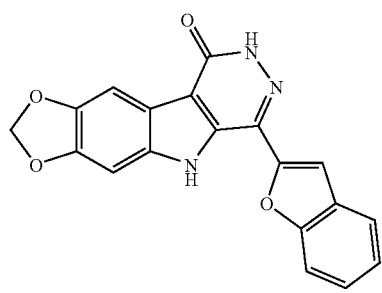

$^1$H NMR (400 MHz, DMSO-d$_6$) δ 12.93 (s, 1H), 12.09 (s, 1H), 7.79 (m, 2H), 7.58 (m, 2H), 7.46 (m, 1H), 7.36 (m, 1H), 7.28 (s, 1H), 6.14 (s, 2H) ppm; MS (m/e) 346 (M+H).

Example 4n

4-Benzofuran-2-yl-9-benzyloxy-2,5-dihydro-pyridazino[4,5-b]indol-1-one

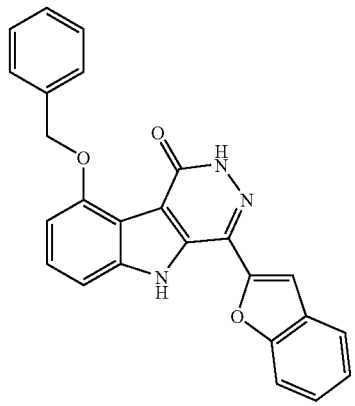

$^1$H NMR (400 MHz, DMSO-d$_6$) δ 12.92 (s, 1H), 12.18 (s, 1H), 7.92 (m, 2H), 7.81 (m, 2H), 7.60 (s, 1H), 7.48-7.23 (m, 7H), 6.95 (m, 1H), 5.35 (s, 2H) ppm; MS (m/e) 408 (M+H).

Example 4o

4-Benzofuran-2-yl-8-benzyloxy-2,5-dihydro-pyridazino[4,5-b]indol-1-one

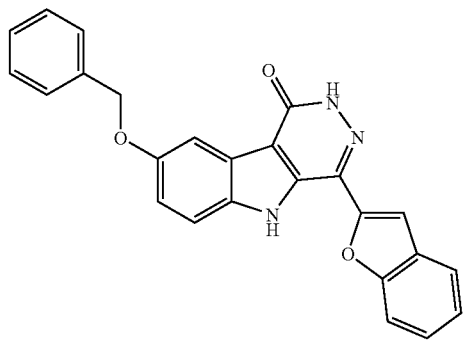

$^1$H NMR (400 MHz, DMSO-d$_6$) δ 13.01 (s, 1H), 12.14 (s, 1H), 7.81-7.74 (m, 4H), 7.63 (s, 1H), 7.53-7.27 (m, 8H), 5.22 (s, 2H) ppm; MS (m/e) 408 (M+H).

Example 4p

4-Benzofuran-2-yl-7-benzyloxy-2,5-dihydro-pyridazino[4,5-b]indol-1-one

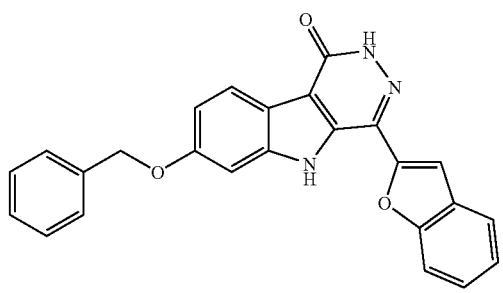

¹H NMR (400 MHz, DMSO-d₆) δ 13.02 (s, 1H), 12.08 (s, 1H), 8.12 (m, 1H), 7.79 (m, 2H), 7.60 (s, 1H), 7.53-7.34 (m, 8H), 7.11 (m, 1H), 5.26 (s, 2H) ppm; MS (m/e) 408 (M+H).

Example 4q

4-Benzofuran-2-yl-8-hydroxy-2,5-dihydro-pyridazino[4,5-b]indol-1-one

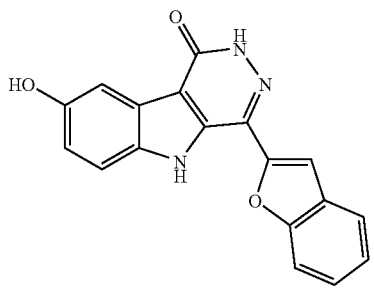

A mixture of Example 4o (68 mg, 0.167 mmol) and 10% Pd/C (20 mg) in THF (10 mL) was hydrogenated at 50 psi for 24 h on a Parr apparatus. The reaction mixture was filtered through a pad of Celite, which was washed with EtOAc. The filtrate was concentrated and dried to give 51 mg (96%) of Example 4q. ¹H NMR (400 MHz, DMSO-d₆) δ 12.91 (s, 1H), 11.97 (s, 1H), 9.34 (s, 1H), 7.79 (m, 2H), 7.65-7.60 (m, 3H), 7.48-7.35 (m, 2H), 7.06 (m, 1H) ppm; MS (m/e) 318 (M+H).

Example 4r 4-(4-Methoxy-phenyl)-2,5-dihydro-pyridazino[4,5-b]indol-1-one

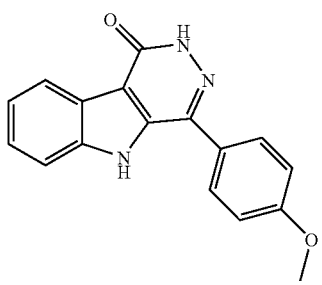

mp>300° C.; ¹H NMR (400 MHz, DMSO-d₆) δ 3.93 (s, 3H), 7.22 (d, J=8.0 Hz, 2H), 7.30 (t, J=8.0 Hz, 1H), 7.48 (t, J=8.0 Hz, 1H), 7.71 (d, J=8.0 Hz, 1H), 7.79 (d, J=8.0 Hz, 2H), 8.20 (d, J=8.0 Hz, 1H), 12.10 (bs, 1H), 12.80, (s, 1H) ppm; MS (m/e) 292 (M+H).

Example 4s 4-(4-Hydroxy-phenyl)-2,5-dihydro-pyridazino[4,5-b]indol-1-one

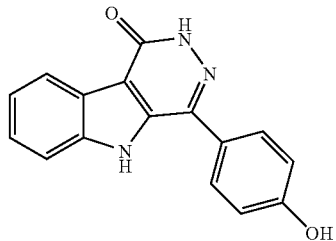

To a slurry of Example 4r (200 mg, 0.69 mmole) in 5 mL CH₂Cl₂ at 0° C. under a nitrogen atmosphere was added IN BBr₃ (4.0 mL). The reaction was warmed to ambient temperature over 18 h. The solids were filtered off and triturated with MeOH to give Example 4s (180 mg) 94% yield: mp>300° C.; ¹H NMR (400 MHz, DMSO-d₆) δ 6.40 (bs, 1H), 6.98 (d, J=8.0 Hz, 2H), 7.32 (t, J=8.0 Hz, 1H), 7.45 (t, J=8.0 Hz, 1H), 7.72 (m, 3H), 8.22 (d, J=8.0 Hz, 1H), 11.98 (s, 1H), 12.71, (s, 1H) ppm; MS (m/e) 278 (M+H).

Example 4t 4-(4-Benzyloxy-phenyl)-7-methoxy-2,5-dihydro-pyridazino[4,5-b]indol-1-one

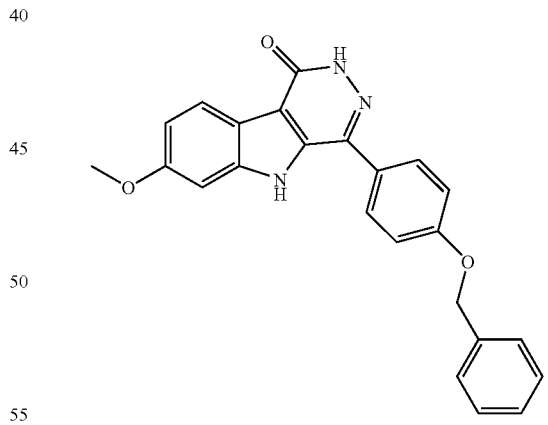

To a slurry of compound 3t (295 mg, 0.53 mmole) in 20 mL MeOH was added hydrazine monohydrate (0.2 mL, 4.4 mmole) and refluxed 18 h. Solids precipitated and were filtered off to yield Example 4t (140 mg, 66%): mp>300° C.; ¹H NMR (400 MHz, DMSO-d₆) δ 3.85 (s, 3H), 5.20 (s, 2H), 6.95 (d, J=8.0 Hz, 1H), 7.10 (d, J=2.0 Hz, 1H), 7.20 (d, J=8.0 Hz, 2H), 7.33 (t, J=8.0 Hz, 1H), 7.40 (t, J=8.0 Hz, 2H), 7.55 (d, J=8.0 Hz, 2H), 7.75 (d, J=8.0 Hz, 2H), 8.05 (d, J=8.0 Hz, 1H), 11.91 (bs, 1H), 12.70, (s, 1H) ppm; MS (m/e) 398 (M+1).

Example 4u 4-(4-Hydroxy-phenyl)-7-methoxy-2,5-dihydro-pyridazino[4,5-b]indol-1-one

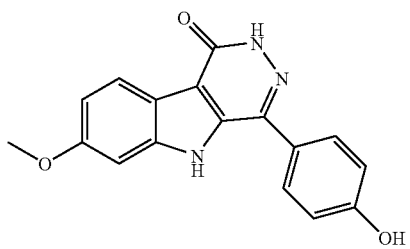

A slurry of Example 4t (120 mg, 0.30 mmol) and 10% Pd/C (12 mg) in 18 mL DMF and 2 mL MeOH was hydrogenated under $H_2$ at 45 psi for 6 h. The mixture was filtered through celite and the solvents removed under vacuum to give Example 4u (33 mg, 35%): mp>300° C.; $^1$H NMR (400 MHz, DMSO-$d_6$) δ 3.87 (s, 3H), 6.95 (d, J=8.0 Hz, 3H), 7.15 (s, 1H), 7.55 (d, J=8.0 Hz, 2H), 8.05 (d, J=8.0 Hz, 1H), 9.75 (s, 1H), 11.80 (s, 1H), 12.55, (s, 1H) ppm; MS (m/e) 308 (M+1).

Example 4v

8-Nitro-4-pyridin-4-yl-2,5-dihydro-pyridazino[4,5-b]indol-1-one

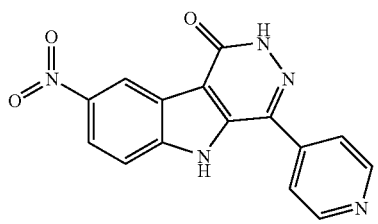

To a stirred solution of Example 4d (50 mg, 0.191 mmol) in acetic acid (10 mL) was added nitric acid (25 μL, 0.392 mmol). The reaction was heated at reflux for 17 h. Additional of nitric acid (400 μL) was added to the reaction and continued to reflux for 3 h. The precipitate was collected, washed with water, diethyl ether, and dried under vacuum at 50° C. to give 48 mg (82%) of Example 4v. $^1$H NMR (400 MHz, DMSO-$d_6$) δ 13.55 (s, 1H), 12.98 (s, 1H), 9.01 (m, 3H), 8.39 (m, 1H), 8.20 (m, 2H), 7.87 (m, 1H) ppm; MS (m/e) 308 (M+H).

The following compounds of formula 11 were prepared by the methods disclosed herein using the general method of Scheme 3 and methods known to one skilled in the art.

Example 11a

4-Benzofuran-2-yl-5-methyl-2,5-dihydro-pyridazino[4,5-b]indol-1-one

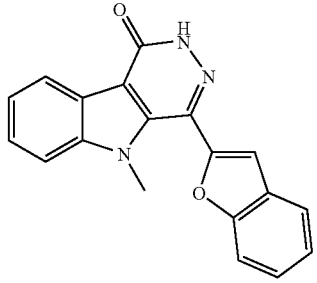

The procedure for Examples 11a and 11b was the same as described in the synthesis for compound 4a and Example 4b.
$^1$H NMR (400 MHz, DMSO-$d_6$) δ 13.21 (s, 1H), 8.30 (m, 1H), 7.82-7.73 (m, 3H), 7.60 (m, 1H), 7.47-7.36 (m, 4H), 3.64 (s, 3H) ppm; MS (m/e) 316 (M+H).

Example 11b

4-Benzo[b]thiophen-2-yl-5-methyl-2,5-dihydro-pyridazino[4,5-b]indol-1-one

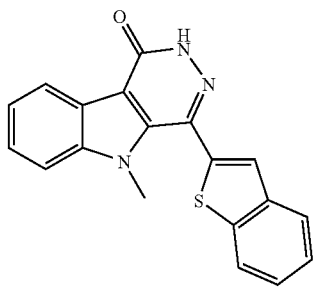

$^1$H NMR (400 MHz, DMSO-$d_6$) δ 13.09 (s, 1H), 8.31 (m, 1H), 8.09 (m, 1H), 7.98 (m, 1H), 7.87 (s, 1H), 7.77 (m, 1H), 7.59 (m, 1H), 7.48 (m, 2H), 7.42 (m, 1H), 3.68 (s, 3H) ppm; MS (m/e) 332 (M+H).

Example 11c

5-Methyl-4-naphthalen-2-yl-2,5-dihydro-pyridazino[4,5-b]indol-1-one

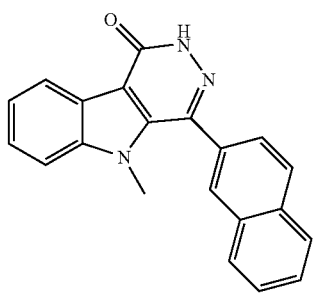

To a stirred solution of methyl 1-methyl-indole-3-carboxylate (1.50 g, 5.31 mmol) in THF (30 mL) was added LDA (4.0 mL, 5.31 mmol) at −78° C. and stirred for 50 min. A solution of naphthalene-2-carbonyl chloride (1.01 g, 5.31 mmol) in THF (12 mL) was added. After 4 h, the reaction was quenched with brine and warmed to room temperature. It was extracted with EtOAc (50 ml×3) and the combined organic extracts were washed with brine, dried (MgSO$_4$), and concentrated in vacuo to gave 1.82 g of crude product 10c. 520 mg of crude product 10c was heated to reflux with H$_2$NNH$_2$.H$_2$O in ethylene glycol (15 mL) for 4 h. After the reaction was cooled to room temperature, the precipitate was collected by filtration, washed with EtOH, dried under vacuum to give 57 mg (12%) of Example 11c. $^1$H NMR (400 MHz, DMSO-d$_6$) δ 12.94 (s, 1H), 8.33 (m, 1H), 8.22 (s, 1H), 8.11-8.05 (m, 3H), 7.79-7.71 (m, 2H), 7.64-7.55 (m, 3H), 7.41 (m, 1H), 3.45 (s, 3H) ppm; MS (m/e) 326 (M+H).

The following compounds of formula 14 were prepared by the methods disclosed herein using the general method of Scheme 4 and methods known to one skilled in the art.

Compound 14a 1-p-Toly-3,5-dihydro-pyridazino[4,5-b]indol-4-one

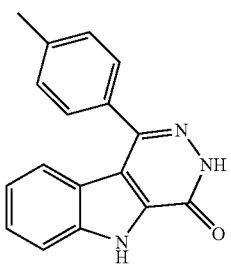

The procedure for compound 14a was the same as described for the synthesis of Example 4a.
$^1$H NMR (400 MHz, DMSO-d$_6$) δ 12.92 (s, 1H), 12.90 (s, 1H), 7.65-7.58 (m, 3H), 7.48-7.39 (m, 4H), 7.16 (m, 1H), 2.45 (s, 3H) ppm; MS (m/e) 276 (M+H).

Example 14b

1-Benzo[b]thiophen-2-yl-3,5-dihydro-pyridazino[4,5-b]indol-4-one

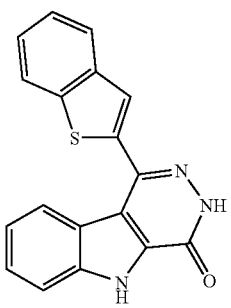

To a stirred solution of indole-2-carboxylic acid ethyl ester (1.0 g, 5.29 mmol) in CH$_2$Cl$_2$ (10 mL) was added tin (IV) chloride (5.82 mL, 5.82 mmol) at 0° C. The reaction was stirred at room temperature for 30 min. A solution of benzo[b]thiophene-2-carbonyl chloride (1.04 g, 5.29 mmol) in CH$_3$NO$_2$ (7.5 mL) was added and stirred for 40 h. The reaction was poured into an ice-water (30 mL) and warmed to room temperature. The reaction mixture was extracted with CH$_2$Cl$_2$ (50 mL×3). The combined organic extracts were washed with brine, dried (MgSO$_4$), and concentrated in vacuo. The residue was purified by flash column chromatography (Hexanes/EtOAc 3:1) to give 1.45 g (78%) of compound 13b. 500 mg of compound 13b was heated to reflux with H$_2$NNH$_2$—H$_2$O in ethylene glycol (10 mL) for 1 h. After cooled to room temperature, the precipitate was collected by filtration, washed with EtOH, dried under vacuum to give 158 mg (35%) of Example 14b. $^1$H NMR (400 MHz, DMSO-d$_6$) δ 13.15 (s, 1H), 13.07 (s, 1H), 8.09-8.02 (m, 3H), 7.95 (m, 1H), 7.69 (m, 1H), 7.55-7.46 (m, 3H), 7.27 (m, 1H) ppm; MS (m/e) 318 (M+1).

The procedure for Example 14c and compound 14d was the same as described for the synthesis of compound 4a.

Example 14c

1-Naphthalen-2-yl-3,5-dihydro-pyridazino[4,5-b]indol-4-one

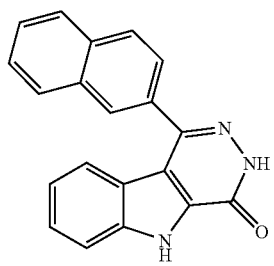

$^1$H NMR (400 MHz, DMSO-d$_6$) δ 13.04 (s, 1H), 12.97 (s, 1H), 8.28 (s, 1H), 8.14 (m, 1H), 8.07 (m, 2H), 7.85 (m, 1H), 7.68-7.62 (m, 3H), 7.48-7.40 (m, 2H), 7.12 (m, 1H) ppm; MS (m/e) 312 (M+H).

Compound 14d 1-(4-methoxy-phenyl)-3,5-dihydro-pyridazino[4,5-b]indol-4-one

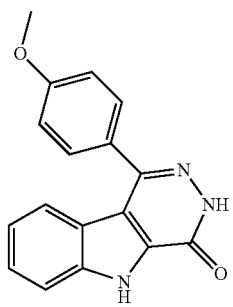

$^1$H NMR (400 MHz, DMSO-d$_6$) δ 12.89 (d, 2H), 7.64 (m, 3H), 7.51-7.45 (m, 2H), 7.19-7.14 (m, 3H), 3.88 (s, 3H) ppm; MS (m/e) 292 (M+1).

Example 14e 1-(4-Hydroxy-phenyl)-3,5-dihydro-pyridazino[4,5-b]indol-4-one

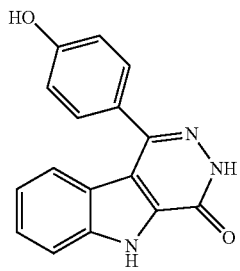

To a stirred solution of compound 14d (100 mg, 0.343 mmol) in methylene chloride (8 mL) at 0° C. was added borotribromide (446 mL, 0.446 mmol). After stirring for 18 h, additional borotribromide (1 mL, 1 mmol) was added, and continued to stir for 54 h. The reaction was carefully quenched with water (10 mL). The precipitation was collected, washed with water, diethyl ether and dried under vacuum to give 91 mg (96%) of Example 14e. $^1$H NMR (400 MHz, DMSO-$d_6$) δ 12.85 (d, 2H), 9.79 (s, 1H), 7.63 (m, 1H), 7.53-7.50 (m, 3H), 7.48-7.44 (m, 1H), 7.19-7.16 (m, 1H), 6.97-6.95 (m, 2H) ppm; MS (m/e) 278 (M+1).

The Examples are set forth in Table I and Table II. These compounds are presented to illustrate the present invention, and are not intended to be limiting thereof.

TABLE I

| Example | $R^1$ | $R^2$ | $R^3$ | $R^4$ | $R^5$ | $R^7$ |
|---------|-------|-------|-------|-------|-------|-------|
| 4b | H | H | H | H | 2-pyridyl | H |
| 4c | H | H | H | H | 3-pyridyl | H |
| 4d | H | H | H | H | 4-pyridyl | H |
| 4e | H | H | H | H | 2,5-dimethylfuran-yl | H |
| 4f | H | H | H | H | 2-thiazolyl | H |
| 4g | H | H | H | H | 1-methylimidazol-2-yl | H |

TABLE I-continued
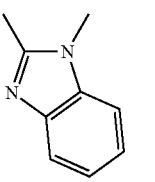
| Example | R¹ | R² | R³ | R⁴ | R⁵ | R⁷ |
|---------|----|----|----|----|----|----|
| 4h | H | H | H | H | 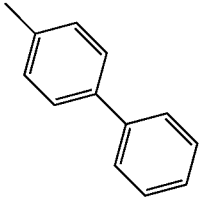 | H |
| 4i | H | H | H | H | 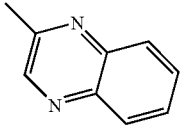 | H |
| 4j | H | H | H | H | 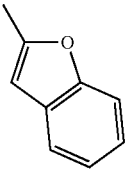 | H |
| 4k | H | H | H | H | 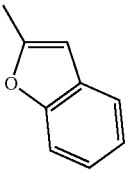 | H |
| 4l | H | —OCH₃ | H | H | 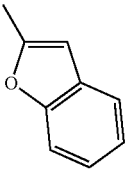 | H |
| 4m | H | —OCH₂O— | H | H | 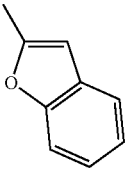 | H |
| 4n | BnO | H | H | H |  | H |

TABLE I-continued
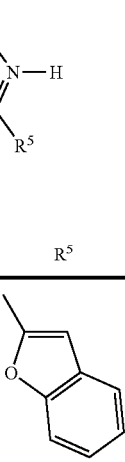
| Example | R¹ | R² | R³ | R⁴ | R⁵ | R⁷ |
|---|---|---|---|---|---|---|
| 4o | H | BnO | H | H | 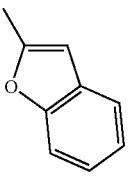 | H |
| 4p | H | H | BnO | H | 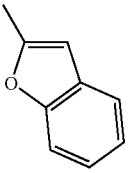 | H |
| 4q | H | OH | H | H | 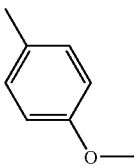 | H |
| 4r | H | H | H | H | 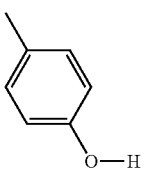 | H |
| 4s | H | H | H | H | 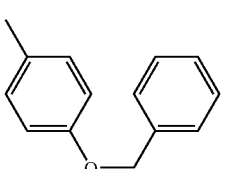 | H |
| 4t | H | H | —OCH₃ | H | 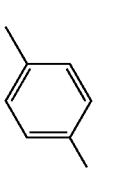 | H |
| 4u | H | H | —OCH₃ | H |  | H |

TABLE I-continued
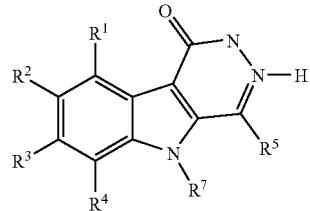
| Example | R¹ | R² | R³ | R⁴ | R⁵ | R⁷ |
|---|---|---|---|---|---|---|
| 4v | H | —NO₂ | H | H | 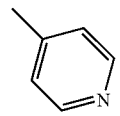 | H |
| 11a | H | H | H | H | 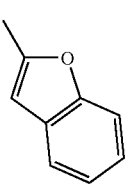 | —CH₃ |
| 11b | H | H | H | H | 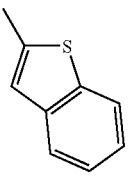 | —CH₃ |
| 11c | H | H | H | H | 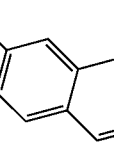 | —CH₃ |
TABLE II
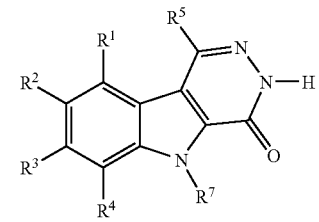
| Example | R¹ | R² | R³ | R⁴ | R⁵ | R⁷ |
|---|---|---|---|---|---|---|
| 14b | H | H | H | H | 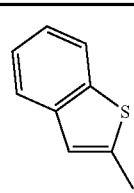 | H |
TABLE II-continued
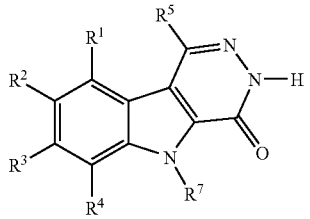
| Example | R¹ | R² | R³ | R⁴ | R⁵ | R⁷ |
|---|---|---|---|---|---|---|
| 14c | H | H | H | H | 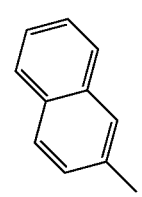 | H |

TABLE II-continued

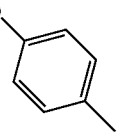

| Example | R¹ | R² | R³ | R⁴ | R⁵ | R⁷ |
|---------|----|----|----|----|----|-----|
| 14e | H | H | H | H | (4-methylphenoxy) | H |

Utility

The compounds of the present invention are useful, inter alia, as therapeutic agents. Particularly, the compounds are useful for kinase inhibition. The compounds of the present invention have been shown to inhibit, for example, one or more of vascular endothelial growth factor receptor (VEGFR) kinase, mixed lineage kinase (MLK), and cyclin-dependent kinase (CDK).

The properties of the compounds of the present invention are beneficial in therapeutic settings. The activities of the fused [d]pyridazin-7-ones of the present invention toward certain enzymes can be exploited to combat the deleterious consequences of these enzymes. Particularly, inhibition of the Vascular Endothelial Growth Factor Receptor (VEGFR) implies utility in, for example, angiogenic disorders, such as cancer of solid tumors, endometriosis, diabetic retinopathy, psoriasis, hemangioblastoma, as well as other ocular diseases and cancers. Inhibition of mixed lineage kinase (MLK) implies utility in, for example, Alzheimer's disease; motor neuron disorders (e.g. amyotrophic lateral sclerosis); Parkinson's disease; cerebrovascular disorders (e.g., stroke, ischaemia); Huntington's disease; AIDS dementia; epilepsy; multiple sclerosis; peripheral neuropathies (e.g., those affecting DRG neurons in chemotherapy-associated peripheral neuropathy) including diabetic neuropathy; disorders induced by excitatory amino acids; and disorders associated with concussive or penetrating injuries of the brain or spinal cord. Inhibition of cyclin-dependent kinase (CDK), implies utility in, for example, hyperproliferative diseases and cancer; and Alzheimer's disease.

Because of their varied utilities, the properties of fused [d]pyridazin-7-ones may be exploited in other settings, such as research. For example, the compounds can be used in the development of in vitro models of neuronal cell survival, function, identification, or for the screening of other synthetic compounds which have activities similar to that of fused [d]pyridazin-7-ones. Thus, the compounds provided by this invention are useful as standard or reference compounds for use in tests or assays for determining the activity of an agent in a pharmaceutical research program.

The compounds can also be utilized to investigate, define and determine molecular targets associated with functional responses. For example, by radiolabelling a fused [d]pyridazin-7-one compound associated with a specific cellular function (e.g., mitogenesis), the target entity to which the derivative binds can be identified, isolated, and purified for characterization. By way of further illustration, compounds may be used in the development of assays and models for further enhancement of the understanding of the roles that inhibition of serine/threonine or tyrosine protein kinases play in the mechanistic aspects of the associated disorders and diseases. Thus, the compounds of the present invention are useful as diagnostic reagents in diagnostic assays, such as the assays described herein.

The inhibition of enzymatic activity by the compounds of the present invention can be determined using, for example, the following assays:
1. Vascular Endothelial Growth Factor Receptor 2 (VEGFR2) kinase inhibition assay;
2. Mixed Lineage Kinase 1 (MLK1) inhibition assay; and
3. Cyclin-Dependent Kinase 5 (CDK5) inhibition assay.

Descriptions of these assays, and the results obtained therein, are set below. The results are intended to be illustrative and not to be construed as limiting the scope of the disclosure. For convenience, certain abbreviations are used to delineate the results which are defined in the body of the text. Others are defined as follows: "µg" for microgram, "mg" for milligram, "g" for gram, "µL" for microliter, "mL" for milliliter, "L" for liter, "nM" for nanomolar, "µM" for micromolar, "mM" for millimolar, "M" for molar, and "nm" for nanometer.

Inhibition of Vascular Endothelial Growth Factor Receptor-2 Kinase Activity

Compounds were tested for their ability to inhibit the kinase activity of recombinant baculovirus-expressed vascular endothelial growth factor receptor-2 (VEGFR2) cytoplasmic domain using the time-resolved fluorescence (TRF) detection system. $IC_{50}$s were conducted in 96-well Costar high binding plates (Corning Costar #3922, Corning, N.Y.). Briefly, each 96-well plate was coated with 100 µL/well of 10 µg/mL recombinant substrate, glutathione S-transferase-phospholipase C-γ fusion protein (GST-PLCγ Lot # 3P5.1A), in Tris-buffered saline (TBS). The VEGFR2 assay mixture (total volume=100 µL/well) consisting of 20 mM HEPES, pH 7.2, 40 µM ATP, 10 mM $MnCl_2$, 0.1% bovine serum albumin (BSA), and test compound (diluted in DMSO; 2.5% DMSO final in assay) was then added to the assay plate. Enzyme (30 ng/mL VEGFR2 Lot #V2g-2.1A) was added and the reaction was allowed to proceed at 37° C. for 15 minutes. Detection of the phosphorylated product was performed by adding 100 µL/well of Eu-N1 labeled PY100 antibody (PerkinElmer Life Sciences #AD0160, Boston, Mass.) diluted 1:5000 in 0.25% BSA in TBS containing 0.05% Tween-20 (TBS-T). Incubation at 37° C. then proceeded for 1 hour, followed by addition of 100 µL enhancement solution (PerkinElmer Life Sciences #1244-105, Boston, Mass.). The plate was gently agitated and after 30 minutes, the fluorescence of the resulting solution was measured using the PerkinElmer EnVision 2100 (or 2102) multilabel plate reader. The results are summarized in Table III.

TABLE III

Inhibitory Effects of fused [d] pyridazin-7-ones on VEGFR-2 Activity

| Compound Number | VEGFR-2 % inhibition @ 300 nM |
|---|---|
| 4b | 7 |
| 4c | 14 |
| 4d | 18 |
| 4e | 4 |
| 4f | 0 |
| 4g | 0 |
| 4h | 0 |
| 4i | 16 |
| 4j | 0 |
| 4k | 0 |
| 4l | 9 |

TABLE III-continued

Inhibitory Effects of fused [d] pyridazin-7-ones on VEGFR-2 Activity

| Compound Number | VEGFR-2 % inhibition @ 300 nM |
|---|---|
| 4m | 0 |
| 4n | 2 |
| 4o | 10 |
| 4p | 14 |
| 4q | 21 |
| 11a | 0 |
| 11b | 0 |
| 11c | 3 |
| 14b | 3 |
| 14c | 1 |

Inhibition of Mixed Lineage Kinase-1 Activity

The activity assay for MLK1 was performed using the 96-well Millipore Multiscreen plate format. Each 50-μL assay mixture contained 50 mM HEPES (pH 7.0), 1 mM EGTA, 10 mM $MgCl_2$, 1 mM DTT, 25 mM β-glycerophosphate, 60 μM ATP, 1 μCi [γ-$^{32}$P]ATP, 0.1% BSA, 500 μg/mL myelin basic protein (Upstate #13-104), 2% DMSO, various concentrations of test compound, and 1 μg/mL of baculoviral GST-MLK1$_{KD}$ (Lot 23.1A). Samples were incubated for 15 minutes at 37° C. The reaction was stopped by adding ice-cold 50% trichloroacetic acid (TCA) and the proteins were allowed to precipitate for 30 minutes at 4° C. The plates were then washed with ice-cold 25% TCA. Supermix scintillation cocktail was added, and the plates were allowed to equilibrate for 1-2 hours prior to counting in the Wallac MicroBeta 1450 Plus scintillation counter. The results are summarized in Table IV.

TABLE IV

Inhibitory Effects of fused [d] pyridazin-7-ones on MLK-1 Activity

| Compound Number | MLK-1 % inhibition @ 1 uM (IC$_{50}$ (nM)) |
|---|---|
| 4b | 0 |
| 4c | 0 |
| 4d | 0 |
| 4e | 10 |
| 4f | 5 |
| 4g | 2 |
| 4h | 0 |
| 4i | 14 |
| 4j | 0 |
| 4k | 41 (2662) |
| 4l | 53 (1020) |
| 4m | 46 |
| 4n | 44 |
| 4o | 73 (381) |
| 4p | 0 |
| 4q | 67 (@300 nM) (138) |
| 11a | 19 |
| 11b | 0 |
| 11c | 0 |
| 14b | 0 |
| 14c | 12 |

Inhibition of Cyclin-Dependent Kinase Activity

Compounds were tested for their ability to inhibit the kinase activity of baculovirus-expressed cyclin-dependent kinase-5 complexed with GST-p25 (CDK5/GST-p25) using a a TRF detection system. Each 96-well Costar high binding plate (Corning Costar #3922, Corning, N.Y.) was coated with 100 μL/well of 50 μg/mL recombinant GST-tagged substrate [GST-retinoblastoma protein (Rb) Lot # 5.1A] in TBS. The CDK5/GST-p25 assay mixture (total volume=100 μL/well) consisting of 20 mM HEPES, pH 7.2, 10 μM ATP, 10 mM $MgCl_2$, 5 mM EGTA, 25 mM β-glycerophosphate, 0.1% BSA, 2.5% DMSO, and various concentrations of test compound were then added to the assay plate. Enzyme (2 ng/mL CDK5/GST-p25 Lot # p25/CD5-3) was added and the reaction was allowed to proceed at 37° C. for 20 minutes. Detection of the phosphorylated product was performed by adding 100 μL/well of phospho-Rb (Ser-780) antibody (Cell Signaling #9307, Beverly, Mass.) diluted 1:10,000 in antibody dilution buffer (0.1% BSA in TBS-T). After 1-hour incubation at room temperature, 100 μL/well of Eu—N1 labelled anti-rabbit antibody diluted 1:50,000 in antibody dilution buffer (PerkinElmer Life Sciences #AD0105, Boston, Mass.) was added. Incubation at room temperature then proceeded for 1 hour, followed by addition of 100 μl enhancement solution (PerkinElmer Life Sciences #1244-105, Boston, Mass.). The plate was gently agitated and after a few minutes, the fluorescence of the resulting solution was measured using the PerkinElmer EnVision 2100 (or 2102) multilabel plate reader. The results are summarized in Table V.

TABLE V

Inhibitory Effects of fused [d] pyridazin-7-ones on CDK-5 Activity

| Compound Number | IC$_{50}$ (nM) |
|---|---|
| 4d | 3818 |
| 4r | >1000 |
| 4s | 657 |
| 4t | >1000 |
| 4u | 756 |
| 4v | >3000 |
| 14e | >3000 |

Dosage and Formulation

For therapeutic purposes, the compounds of the present invention can be administered by any means that results in the contact of the active agent with the agent's site of action in the body of a mammal. The compounds may be administered by any conventional means available for use in conjunction with pharmaceuticals, either as individual therapeutic agents or in a combination of therapeutic agents. They are preferably administered as the sole active agent in a pharmaceutical composition, but alternatively, they can be used in combination with other active ingredients, e.g., other growth factors which facilitate neuronal survival or axonal regeneration in diseases or disorders. The compounds are preferably combined with a pharmaceutical carrier selected on the basis of the chosen route of administration and standard pharmaceutical practice.

The compounds can be formulated into pharmaceutical compositions, for example, by admixture with pharmaceutically acceptable nontoxic excipients and carriers. Such compositions can be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, transdermal patches.

The composition can be conveniently administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds.

Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for trans-dermal patches are preferably lipophilic emulsions.

Compounds of Formula I and pharmaceutically acceptable salts thereof can be administered orally or non-orally, e.g., as an ointment or an injection. The concentrations of the compounds of this invention in a therapeutic composition can vary. The concentration will depend upon factors such as the total dosage of the drug to be administered, the chemical characteristics (e.g., hydrophobicity) of the compounds employed, the route of administration, the age, body weight and symptoms of a patient, etc. The compounds of this invention may be provided in an aqueous physiological buffer solution containing about 0.1 to 10% w/v compound for parenteral administration. Typical dose ranges are from about 1 mg to about 1 μg/kg of body weight per day; a preferred dose range is from about 0.01 mg/kg to 100 mg/kg of body weight per day, and preferably about 0.1 to 20 mg/kg once to four times per day. A preferred dosage of drug to be administered is likely to depend on variables such as the type and extent of progression of the disease or disorder, the overall health status of the particular patient, the relative biological efficacy of the compound selected, and formulation of the compound excipient, and its route of administration.

The pharmaceutical compositions in accordance with the present invention can be prepared by uniformly mixing an effective amount of a compound of Formula I or a pharmaceutically acceptable salt thereof, as an active ingredient, with a pharmaceutically acceptable carrier. The carrier may take a wide range of forms according to the forms of composition suitable for administration. It is desired that such pharmaceutical compositions are prepared in a unit dose form suitable for oral or non-oral administration. The forms for non-oral administration include ointment and injection.

Tablets can be prepared using excipients such as lactose, glucose, sucrose, mannitol and methyl cellulose, disintegrating agents such as starch, sodium alginate, calcium carboxymethyl cellulose and crystalline cellulose, lubricants such as magnesium stearate and talc, binders such as gelatin, polyvinyl alcohol, polyvinyl pyrrolidone, hydroxypropyl cellulose and methyl cellulose, surfactants such as sucrose fatty acid ester and sorbitol fatty acid ester, and the like in a conventional manner. It is preferred that each tablet contains 15-300 mg of the active ingredient.

Granules can be prepared using excipients such as lactose and sucrose, disintegrating agents such as starch, binders such as gelatin, and the like in a conventional manner. Powders can be prepared using excipients such as lactose and mannitol, and the like in a conventional manner. Capsules can be prepared using gelatin, water, sucrose, gum arabic, sorbitol, glycerin, crystalline cellulose, magnesium stearate, talc, and the like in a conventional manner. It is preferred that each capsule contains 15-300 mg of the active ingredient.

Syrup preparations can be prepared using sugars such as sucrose, water, ethanol, and the like in a conventional manner.

Ointment can be prepared using ointment bases such as vaseline, liquid paraffin, lanolin and macrogol, emulsifiers such as sodium lauryl lactate, benzalkonium chloride, sorbitan mono-fatty acid ester, sodium carboxymethyl cellulose and gum arabic, and the like in a conventional manner.

Injectable preparations can be prepared using solvents such as water, physiological saline, vegetable oils (e.g., olive oil and peanut oil), ethyl oleate and propylene glycol, solubilizing agents such as sodium benzoate, sodium salicylate and urethane, isotonicity agents such as sodium chloride and glucose, preservatives such as phenol, cresol, p-hydroxybenzoic ester and chlorobutanol, antioxidants such as ascorbic acid and sodium pyrosulfite, and the like in a conventional manner.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed is:

1. A compound of Formula (II):

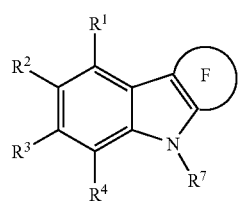

wherein:

ring F is:

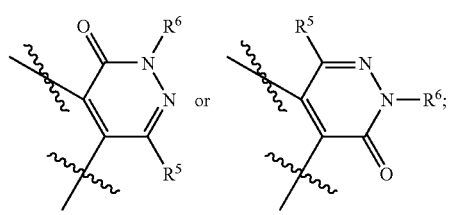

$R^1$ is selected from:
(a) hydrogen, $C_1$-$C_6$ alkyl substituted with 0 to 3 $R^{10}$ groups, $C_2$-$C_6$ alkenyl substituted with 0 to 3 $R^{10}$ groups, $C_2$-$C_6$ alkynyl substituted with 0 to 3 $R^{10}$ groups, $C_6$-$C_{12}$ aryl substituted with 0 to 3 $R^{10}$ groups, $C_3$-$C_7$ cycloalkyl substituted with 0 to 3 $R^{10}$ groups, $C_5$-$C_{10}$ heterocyclyl substituted with 0 to 3 $R^{10}$ groups, $C_5$-$C_{10}$ heteroaryl substituted with 0 to 3 $R^{10}$ groups;

(b) halogen, —$CF_3$, —$CHF_2$, —$C\equiv N$, —CHO, —$O(CR^a{}_2)_nR^8$, —$(CR^a{}_2)_nC(=O)(CR^a{}_2)_nR^8$, —$(CR^a{}_2)_nC(=O)(CR^a{}_2)_nOR^8$, —$(CR^a{}_2)_nSi(R^8)_3$, —$(CR^a{}_2)_nNO_2$, —$(CR^a{}_2)_nN(R^b)(R^c)$, —$(CR^a{}_2)_nC(=O)N(R^b)(R^c)$, —$(CR^a{}_2)_nOC(=O)N(R^b)(R^c)$, —$(CR^a{}_2)_nOC(=O)(CR^a{}_2)_nR^8$, —$(CR^a{}_2)_nN(R^b)C(=O)R^8$, —$(CR^a{}_2)_nNC(=O)N(R^b)(R^c)$, —$(CR^a{}_2)_nNC(=O)OR^8$, and —$(CR^a{}_2)_nNS(O)_xR^8$;

$R^4$ is selected from hydrogen, halogen, $C_1$-$C_4$ alkyl, and —$O(CR^a{}_2)_nR^8$;

$R^2$ and $R^3$ together form a methylenedioxy or an ethylenedioxy group;

$R^5$ is selected from $C_3$-$C_7$ cycloalkyl substituted with 0 to 3 $R^9$ groups and $C_5$-$C_{10}$ heterocyclyl substituted with 0 to 3 $R^9$ groups;

$R^6$ is hydrogen;

$R^7$ is selected from hydrogen and methyl;

$R^8$ is selected from hydrogen, $C_1$-$C_4$ alkyl, $C_2$-$C_4$ alkenyl, $C_2$-$C_4$ alkynyl, $C_6$-$C_{12}$ aryl, $C_3$-$C_7$ cycloalkyl, $C_5$-$C_{10}$ heterocyclyl, and $C_5$-$C_{10}$ heteroaryl;

$R^9$ is selected from:

(a) $C_1$-$C_6$ alkyl, $C_2$-$C_6$ alkenyl, $C_2$-$C_6$ alkynyl, $C_6$-$C_{12}$ aryl, $C_3$-$C_7$ cycloalkyl, $C_5$-$C_{10}$ heterocyclyl, $C_5$-$C_{10}$ heteroaryl, (b) halogen, —$CF_3$, —$CHF_2$, —$C\equiv N$, —CHO, (c) —$O(CR^a{}_2)_nR^8$, —$(CR^a{}_2)_nC(=O)(CR^a{}_2)_nR^8$, —$(CR^a{}_2)_nC(=O)(CR^a{}_2)_nOR^8$, —$(CR^a{}_2)_nSi(R^8)_3$, —$(CR^a{}_2)_nNO_2$, —$(CR^a{}_2)_nN(R^b)(R^c)$, —$(CR^a{}_2)_nC(=O)N(R^b)(R^c)$, —$(CR^a{}_2)_nOC(=O)N(R^b)(R^c)$, —$(CR^a{}_2)_nOC(=O)(CR^a{}_2)_nR^8$, —$(CR^a{}_2)_nN(R^b)C(=O)R^8$, —$(CR^a{}_2)_nNC(=O)N(R^b)(R^c)$, —$(CR^a{}_2)_nNC(=O)OR^8$, and —$(CR^a{}_2)_nNS(O)_xR^8$;

$R^{10}$ is selected from $C_1$-$C_6$ alkyl, $C_2$-$C_6$ alkenyl, $C_2$-$C_6$ alkynyl, halogen, and —$OR^{11}$;

$R^{11}$ is selected from hydrogen, $C_1$-$C_4$ alkyl, $C_2$-$C_4$ alkenyl, $C_2$-$C_4$ alkynyl, $C_6$-$C_{12}$ aryl, $C_3$-$C_7$ cycloalkyl, $C_5$-$C_{10}$ heterocyclyl, and $C_5$-$C_{10}$ heteroaryl;

$R^a$ is selected from hydrogen, $C_1$-$C_4$ alkyl, $C_2$-$C_4$ alkenyl, and $C_2$-$C_4$ alkynyl;

$R^b$ and $R^c$ are independently selected from hydrogen, hydroxy, $C_1$-$C_4$ alkyl, $C_2$-$C_4$ alkenyl, and $C_2$-$C_4$ alkynyl;

n is independently at each occurrence 0, 1, 2, 3 or 4; and x is independently 1 or 2.

2. A compound of Formula (II):

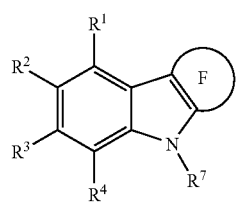

(II)

wherein:

ring F is:

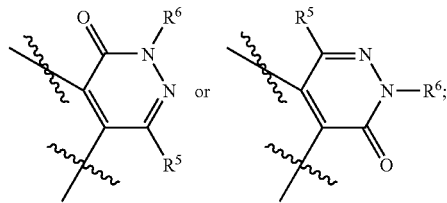

$R^1$ is selected from:

(a) hydrogen, $C_1$-$C_6$ alkyl substituted with 0 to 3 $R^{10}$ groups, $C_2$-$C_6$ alkenyl substituted with 0 to 3 $R^{10}$ groups, $C_2$-$C_6$ alkynyl substituted with 0 to 3 $R^{10}$ groups, $C_6$-$C_{12}$ aryl substituted with 0 to 3 $R^{10}$ groups, $C_3$-$C_7$ cycloalkyl substituted with 0 to 3 $R^{10}$ groups, $C_5$-$C_{10}$ heterocyclyl substituted with 0 to 3 $R^{10}$ groups, $C_5$-$C_{10}$ heteroaryl substituted with 0 to 3 $R^{10}$ groups;

(b) halogen, —$CF_3$, —$CHF_2$, —$C\equiv N$, —CHO, —$O(CR^a{}_2)_nR^8$, —$(CR^a{}_2)_nC(=O)(CR^a{}_2)_nR^8$, —$(CR^a{}_2)_nC(=O)(CR^a{}_2)_nOR^8$, —$(CR^a{}_2)_nSi(R^8)_3$, —$(CR^a{}_2)_nNO_2$—$(CR^a{}_2)_nN(R^b)(R^c)$, —$(CR^a{}_2)_nC(=O)N(R^b)(R^c)$, —$(CR^a{}_2)_nOC(=O)N(R^b)(R^c)$, —$(CR^a{}_2)_nOC(=O)(CR^a{}_2)_nR^8$, —$(CR^a{}_2)_nN(R^b)C(=O)R^8$, —$(CR^a{}_2)_nNC(=O)N(R^b)(R^c)$, —$(CR^a{}_2)_nNC(=O)OR^8$, and —$(CR^a{}_2)_nNS(O)_xR^8$;

$R^4$ is selected from hydrogen, halogen, $C_1$-$C_4$ alkyl, and —$O(CR^a{}_2)_nR^8$;

$R^2$ and $R^3$ together form a methylenedioxy or an ethylenedioxy group;

$R^5$ is $C_5$-$C_{10}$ heteroaryl substituted with 0 to 3 $R^9$ groups;

$R^6$ is hydrogen;

$R^7$ is selected from hydrogen and methyl;

$R^8$ is selected from hydrogen, $C_1$-$C_4$ alkyl, $C_2$-$C_4$ alkenyl, $C_2$-$C_4$ alkynyl, $C_6$-$C_{12}$ aryl, $C_3$-$C_7$ cycloalkyl, $C_5$-$C_{10}$ heterocyclyl, and $C_5$-$C_{10}$ heteroaryl;

$R^9$ is selected from:

(a) $C_1$-$C_6$ alkyl, $C_2$-$C_6$ alkenyl, $C_2$-$C_6$ alkynyl, $C_6$-$C_{12}$ aryl, $C_3$-$C_7$ cycloalkyl, $C_5$-$C_{10}$ heterocyclyl, $C_5$-$C_{10}$ heteroaryl, (b) halogen, —$CF_3$, —$CHF_2$, —$C\equiv N$, —CHO, (c) —$O(CR^a{}_2)_nR^8$, —$(CR^a{}_2)_nC(=O)(CR^a{}_2)_nR^8$, —$(CR^a{}_2)_nC(=O)(CR^a{}_2)_nOR^8$, —$(CR^a{}_2)_nSi(R^8)_3$, —$(CR^a{}_2)_nNO_2$, —$(CR^a{}_2)_nN(R^b)(R^c)$, —$(CR^a{}_2)_nC(=O)N(R^b)(R^c)$, —$(CR^a{}_2)_nOC(=O)N(R^b)(R^c)$, —$(CR^a{}_2)_nOC(=O)(CR^a{}_2)_nR^8$, —$(CR^a{}_2)_nN(R^b)C(=O)R^8$, —$(CR^a{}_2)_nNC(=O)N(R^b)(R^c)$, —$(CR^a{}_2)_nNC(=O)OR^8$, and —$(CR^a{}_2)_nNS(O)_xR^8$;

$R^{10}$ is selected from $C_1$-$C_6$ alkyl, $C_2$-$C_6$ alkenyl, $C_2$-$C_6$ alkynyl, halogen, and —$OR^{11}$;

$R^{11}$ is selected from hydrogen, $C_1$-$C_4$ alkyl, $C_2$-$C_4$ alkenyl, $C_2$-$C_4$ alkynyl, $C_6$-$C_{12}$ aryl, $C_3$-$C_7$ cycloalkyl, $C_5$-$C_{10}$ heterocyclyl, and $C_5$-$C_{10}$ heteroaryl;

$R^a$ is selected from hydrogen, $C_1$-$C_4$ alkyl, $C_2$-$C_4$ alkenyl, and $C_2$-$C_4$ alkynyl;

$R^b$ and $R^c$ are independently selected from hydrogen, hydroxy, $C_1$-$C_4$ alkyl, $C_2$-$C_4$ alkenyl, and $C_2$-$C_4$ alkynyl;

n is independently at each occurrence 0, 1, 2, 3 or 4; and x is independently 1 or 2.

3. A compound of Formula (II):

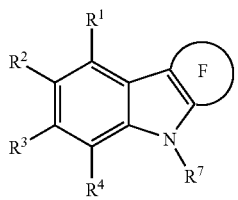

wherein:
ring F is:

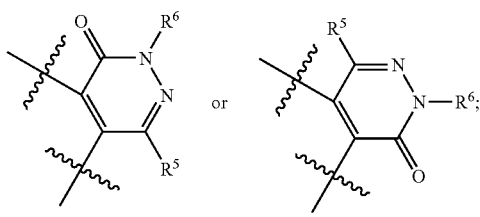

$R^1$ and $R^2$ are independently selected from:
(a) hydrogen, $C_1$-$C_6$ alkyl substituted with 0 to 3 $R^{10}$ groups, $C_2$-$C_6$ alkenyl substituted with 0 to 3 $R^{10}$ groups, $C_2$-$C_6$ alkynyl substituted with 0 to 3 $R^{10}$ groups, $C_6$-$C_{12}$ aryl substituted with 0 to 3 $R^{10}$ groups, $C_3$-$C_7$ cycloalkyl substituted with 0 to 3 $R^{10}$ groups, $C_5$-$C_{10}$ heterocyclyl substituted with 0 to 3 $R^{10}$ groups, $C_5$-$C_{10}$ heteroaryl substituted with 0 to 3 $R^{10}$ groups;
(b) halogen, —$CF_3$, —$CHF_2$, —C≡N, —CHO, —O($CR^a_2$)$_n$$R^8$, —($CR^a_2$)$_n$C(=O)($CR^a_2$)$_n$$R^8$, —($CR^a_2$)$_n$C(=O)($CR^a_2$)$_n$$OR^8$, —($CR^a_2$)$_n$Si($R^8$)$_3$, —($CR^a_2$)$_n$$NO_2$, —($CR^a_2$)$_n$N($R^b$)($R^c$), —($CR^a_2$)$_n$C(=O)N($R^b$)($R^c$), —($CR^a_2$)$_n$OC(=O)N($R^b$)($R^c$), —($CR^a_2$)$_n$OC(=O)($CR^a_2$)$_n$$R^8$, —($CR^a_2$)$_n$N($R^b$)C(=O)$R^8$, —($CR^a_2$)$_n$NC(=O)N($R^b$)($R^c$), —($CR^a_2$)$_n$NC(=O)$OR^8$, —($CR^a_2$)$_n$NS(O)$_x$$R^8$; and
(c) a group wherein $R^1$ and $R^2$ together form a methylenedioxy or an ethylenedioxy group;

$R^3$ and $R^4$ are independently selected from hydrogen, halogen, $C_1$-$C_4$ alkyl, and —O($CR^a_2$)$_n$$R^8$;
alternatively, $R^2$ and $R^3$ together form a methylenedioxy or an ethylenedioxy group;
$R^5$ is benzofuranyl substituted with 0 to 3 $R^9$ groups;
$R^6$ is hydrogen;
$R^7$ is selected from hydrogen and methyl;
$R^8$ is selected from hydrogen, $C_1$-$C_4$ alkyl, $C_2$-$C_4$ alkenyl, $C_2$-$C_4$ alkynyl, $C_6$-$C_{12}$ aryl, $C_3$-$C_7$ cycloalkyl, $C_5$-$C_{10}$ heterocyclyl, and $C_5$-$C_{10}$ heteroaryl;
$R^9$ is selected from:
(a) $C_1$-$C_6$ alkyl, $C_2$-$C_6$ alkenyl, $C_2$-$C_6$ alkynyl, $C_6$-$C_{12}$ aryl, $C_3$-$C_7$ cycloalkyl, $C_5$-$C_{10}$ heterocyclyl, $C_5$-$C_{10}$ heteroaryl,
(b) halogen, —$CF_3$, —$CHF_2$, —C≡N, —CHO,
(c) —O($CR^a_2$)$_n$$R^8$, —($CR^a_2$)$_n$C(=O)($CR^a_2$)$_n$$R^8$, —($CR^a_2$)$_n$C(=O)($CR^a_2$)$_n$$OR^8$, —($CR^a_2$)$_n$Si($R^8$)$_3$, —($CR^a_2$)$_n$$NO_2$, —($CR^a_2$)$_n$N($R^b$)($R^c$), —($CR^a_2$)$_n$C(=O)N($R^b$)($R^c$), —($CR^a_2$)$_n$OC(=O)N($R^b$)($R^c$), —($CR^a_2$)$_n$OC(=O)($CR^a_2$)$_n$$R^8$, —($CR^a_2$)$_n$N($R^b$)C(=O)$R^8$, —($CR^a_2$)$_n$NC(=O)N($R^b$)($R^c$), —($CR^a_2$)$_n$NC(=O)$OR^8$, and —($CR^a_2$)$_n$NS(O)$_x$$R^8$;
$R^{10}$ is setected from $C_1$-$C_6$ alkyl, $C_2$-$C_6$ alkenyl, $C_2$-$C_6$ alkynyl, halogen, and —$OR^{11}$;
$R^{11}$ is selected from hydrogen, $C_1$-$C_4$ alkyl, $C_2$-$C_4$ alkenyl, $C_2$-$C_4$ alkynyl, $C_6$-$C_{12}$ aryl, $C_3$-$C_7$ cycloalkyl, $C_5$=$C_{10}$ heterocyclyl, and $C_5$-$C_{10}$ heteroaryl;
$R^a$ is selected from hydrogen, $C_1$-$C_4$ alkyl, $C_2$-$C_4$ alkenyl, and $C_2$-$C_4$ alkynyl;
$R^b$ and $R^c$ are independently selected from hydrogen, hydroxy, $C_1$-$C_4$ alkyl, $C_2$-$C_4$ alkenyl, and $C_2$-$C_4$ alkynyl;
n is independently at each occurrence 0, 1, 2, 3 or 4; and
x is independently 1 or 2.

4. A compound as described in Table I:

TABLE I

| Example | $R^1$ | $R^2$ | $R^3$ | $R^4$ | $R^5$ | $R^7$ |
|---|---|---|---|---|---|---|
| 4b | H | H | H | H | 2-pyridyl | H |
| 4c | H | H | H | H | 3-pyridyl | H |

TABLE I-continued
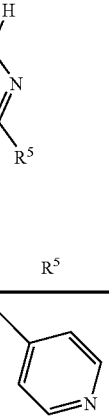
| Example | R¹ | R² | R³ | R⁴ | R⁵ | R⁷ |
|---------|----|----|----|----|----|----|
| 4d | H | H | H | H | 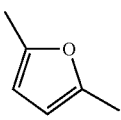 | H |
| 4e | H | H | H | H | 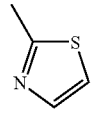 | H |
| 4f | H | H | H | H | 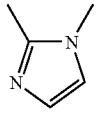 | H |
| 4g | H | H | H | H | 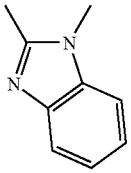 | H |
| 4h | H | H | H | H | 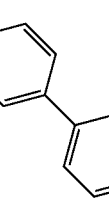 | H |
| 4i | H | H | H | H | 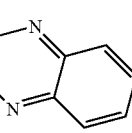 | H |
| 4j | H | H | H | H | 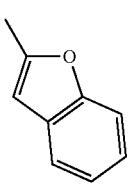 | H |
| 4k | H | H | H | H |  | H |

TABLE I-continued
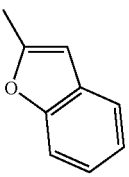
| Example | R¹ | R² | R³ | R⁴ | R⁵ | R⁷ |
|---|---|---|---|---|---|---|
| 4l | H | —OCH₃ | H | H | 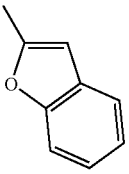 | H |
| 4m | H | —OCH₂O— | | H | 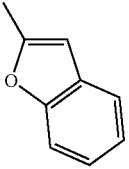 | H |
| 4n | BnO | H | H | H | 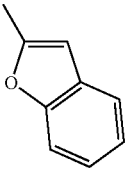 | H |
| 4o | H | BnO | H | H | 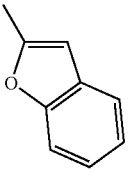 | H |
| 4p | H | H | BnO | H | 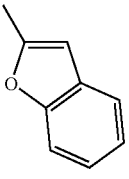 | H |
| 4q | H | OH | H | H | 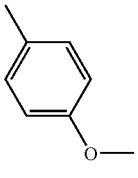 | H |
| 4r | H | H | H | H |  | H |

TABLE I-continued

| Example | R¹ | R² | R³ | R⁴ | R⁵ | R⁷ |
|---------|----|----|----|----|----|----|
| 4s | H | H | H | H | 4-hydroxyphenyl | H |
| 4t | H | H | —OCH₃ | H | 4-(benzyloxy)phenyl | H |
| 4u | H | H | —OCH₃ | H | 4-hydroxyphenyl | H |
| 4v | H | —NO₂ | H | H | pyridin-4-yl | H |
| 11a | H | H | H | H | benzofuran-2-yl | —CH₃ |
| 11b | H | H | H | H | benzothiophen-2-yl | —CH₃ |
| 11c | H | H | H | H | naphthalen-2-yl | —CH₃ | or a stereoisomer or pharmaceutically acceptable salt form thereof

5. A compound as described in Table II:

TABLE II

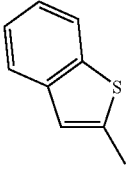

| Example | R¹ | R² | R³ | R⁴ | R⁵ | R⁷ |
|---|---|---|---|---|---|---|
| 14b | H | H | H | H | 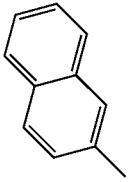 | H |
| 14c | H | H | H | H | 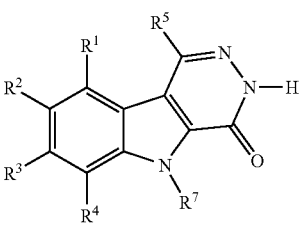 | H |

TABLE II-continued

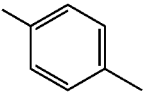

| Example | R¹ | R² | R³ | R⁴ | R⁵ | R⁷ |
|---|---|---|---|---|---|---|
| 14e | H | H | H | H | H—O—⟨aryl⟩ | H | or a stereoisomer or pharmaceutically acceptable salt form thereof.

6. A pharmaceutical composition comprising a compound of claim 4 and a pharmaceutically acceptable carrier.

7. A pharmaceutical composition comprising a compound of claim 5 and a pharmaceutically acceptable carrier.

* * * * *